United States Patent
Lam et al.

(10) Patent No.: US 10,254,616 B2
(45) Date of Patent: Apr. 9, 2019

(54) VARIABLE TRANSMITTANCE OPTICAL FILTER WITH SUBSTANTIALLY CO-PLANAR ELECTRODE SYSTEM

(71) Applicant: Switch Materials, Inc., Burnaby (CA)

(72) Inventors: Duhane Lam, Vancouver (CA); Neil Robin Branda, North Vancouver (CA)

(73) Assignee: SWITCH MATERIALS, INC., Burnaby, British Columbia (CA)

( * ) Notice: Subject to any disclaimer, the term of this patent is extended or adjusted under 35 U.S.C. 154(b) by 49 days.

(21) Appl. No.: 15/392,658

(22) Filed: Dec. 28, 2016

(65) Prior Publication Data

US 2017/0108753 A1    Apr. 20, 2017

Related U.S. Application Data

(63) Continuation of application No. 14/932,602, filed on Nov. 4, 2015, now Pat. No. 9,568,799, which is a
(Continued)

(51) Int. Cl.
*G02F 1/155*    (2006.01)
*G02F 1/15*    (2006.01)
(Continued)

(52) U.S. Cl.
CPC ........... *G02F 1/155* (2013.01); *C07D 495/04* (2013.01); *E06B 9/24* (2013.01); *G02B 5/23* (2013.01);
(Continued)

(58) Field of Classification Search
CPC ........ G02F 1/0102; G02F 1/15; G02F 1/1506; G02F 1/155; G02F 1/163;
(Continued)

(56) References Cited

U.S. PATENT DOCUMENTS

| | | | |
|---|---|---|---|
| 3,813,142 A | 5/1974 | Buhrer | |
| 4,054,362 A | 10/1977 | Baues | |

(Continued)

FOREIGN PATENT DOCUMENTS

| | | | |
|---|---|---|---|
| JP | 57-167009 A | 10/1982 | |
| JP | 08-160471 A | 6/1996 | |

(Continued)

OTHER PUBLICATIONS

Office Action issued in corresponding European Patent Application No. 11 849 064.8, dated Sep. 14, 2017, 6 pages.

(Continued)

*Primary Examiner* — Loha Ben
(74) *Attorney, Agent, or Firm* — Merchant & Gould P.C.

(57) ABSTRACT

A variable transmittance optical filter comprising: a first layer comprising a first substantially transparent substrate with a substantially co-planar (SC) electrode system disposed thereon, the SC electrode system made of transparent electrically conductive material and comprising at least one pair of electrically separate electrodes arranged in a substantially co-planar manner on the first substantially transparent substrate, each pair of electrically separate electrodes comprising a first electrode and a second electrode, a second layer proximate to the first layer and comprising a transition material that darkens in response to a non-electrical stimulus and lightens in response to application of an electric voltage; and an electrical connection system for electrically connecting the SC electrode system to a source of electric voltage.

15 Claims, 7 Drawing Sheets

Related U.S. Application Data continuation of application No. 13/994,409, filed as application No. PCT/CA2011/001378 on Dec. 15, 2011, now abandoned.

(60) Provisional application No. 61/423,536, filed on Dec. 15, 2010.

(51) Int. Cl.
| | |
|---|---|
| *G02B 5/23* | (2006.01) |
| *G02C 7/10* | (2006.01) |
| *E06B 9/24* | (2006.01) |
| *C07D 495/04* | (2006.01) |
| *G02F 1/03* | (2006.01) |
| *G02F 1/163* | (2006.01) |
| *G09G 3/38* | (2006.01) |
| *G02F 1/01* | (2006.01) |
| *G02F 1/1506* | (2019.01) |
| *G02F 1/153* | (2006.01) |

(52) U.S. Cl.
CPC ............ *G02C 7/101* (2013.01); *G02C 7/102* (2013.01); *G02F 1/0126* (2013.01); *G02F 1/03* (2013.01); *G02F 1/15* (2013.01); *G02F 1/1506* (2013.01); *G02F 1/163* (2013.01); *G09G 3/38* (2013.01); *C08G 2261/54* (2013.01); *E06B 2009/247* (2013.01); *E06B 2009/2417* (2013.01); *E06B 2009/2464* (2013.01); *G02F 1/153* (2013.01); *G02F 2001/1512* (2013.01); *G02F 2001/1552* (2013.01); *G02F 2001/1557* (2013.01); *G02F 2201/124* (2013.01)

(58) Field of Classification Search
CPC ..... G02F 2001/1512; G02F 2001/1552; G02F 1/0126; G02F 2001/1557; G02B 5/23; B60J 3/04; E06B 9/24; E06B 2009/247; E06B 2009/2417; E06B 2009/2464; G09G 3/34; G09G 3/3433; G09G 3/38; G02C 7/101; G02C 7/102; C07D 495/04; C09K 9/02; C08G 2261/54
USPC ....... 359/241, 242, 244, 245, 265, 273, 275; 345/105; 29/846, 847, 874; 156/99
See application file for complete search history.

(56) References Cited

U.S. PATENT DOCUMENTS

| | | | |
|---|---|---|---|
| 4,857,908 A | 8/1989 | Kogure et al. | |
| 5,355,245 A | 10/1994 | Lynam | |
| 5,384,653 A | 1/1995 | Benson et al. | |
| 5,463,491 A | 10/1995 | Check, III | |
| 5,604,626 A | 2/1997 | Teowee et al. | |
| 5,838,483 A | 11/1998 | Teowee et al. | |
| 6,055,088 A | 4/2000 | Fix et al. | |
| 6,055,089 A * | 4/2000 | Schulz ................... | G02F 1/163 136/251 |
| 6,065,836 A | 5/2000 | Krishnan et al. | |
| 6,084,702 A | 7/2000 | Byker et al. | |
| 6,246,505 B1 | 6/2001 | Teowee et al. | |
| 6,317,248 B1 | 11/2001 | Agrawal et al. | |
| 6,369,934 B1 | 4/2002 | Bechinger et al. | |
| 6,449,082 B1 | 9/2002 | Agrawal et al. | |
| 6,597,489 B1 | 7/2003 | Guarr et al. | |
| 6,606,184 B2 | 8/2003 | Guarr et al. | |
| 6,906,842 B2 | 6/2005 | Agrawal et al. | |
| 6,910,729 B2 | 6/2005 | Kraenzler et al. | |
| 6,934,067 B2 | 8/2005 | Ash et al. | |
| 7,300,167 B2 | 11/2007 | Fernando et al. | |
| 7,323,634 B2 | 1/2008 | Speakman | |
| 7,459,189 B2 | 12/2008 | Tahara et al. | |
| 7,777,055 B2 * | 8/2010 | Branda ................ | C07D 495/04 549/49 |
| 8,379,288 B2 | 2/2013 | Duluard et al. | |
| 8,441,707 B2 * | 5/2013 | Lam ......................... | G02B 5/23 359/241 |
| 8,643,930 B2 * | 2/2014 | Gillaspie ............... | G02F 1/1525 359/265 |
| 8,687,258 B2 | 4/2014 | Lam et al. | |
| 9,176,357 B2 * | 11/2015 | Lam .......................... | B60J 3/04 |
| 9,568,799 B2 * | 2/2017 | Lam .......................... | E06B 9/24 |
| 2002/0005977 A1 | 1/2002 | Guarr et al. | |
| 2006/0007519 A1 | 1/2006 | Kanouni et al. | |
| 2006/0209007 A1 | 9/2006 | Pyo et al. | |
| 2007/0097484 A1 | 5/2007 | Libretto et al. | |
| 2007/0128905 A1 | 6/2007 | Speakman | |
| 2007/0153355 A1 | 7/2007 | Huang et al. | |
| 2007/0220427 A1 | 9/2007 | Briancon et al. | |
| 2008/0239452 A1 | 10/2008 | Xu et al. | |
| 2009/0002802 A1 | 1/2009 | Shibuya et al. | |
| 2010/0266801 A1 | 10/2010 | Jahoda et al. | |
| 2010/0301471 A1 | 12/2010 | Simin et al. | |
| 2013/0278989 A1 | 10/2013 | Lam et al. | |

FOREIGN PATENT DOCUMENTS

| | | |
|---|---|---|
| WO | 02/18132 A2 | 3/2002 |
| WO | 2004/015024 A1 | 2/2004 |
| WO | 2006/125317 A1 | 11/2006 |
| WO | 2009/087575 A2 | 7/2009 |
| WO | 2012/125348 A2 | 9/2012 |
| WO | 2010/040954 A1 | 4/2013 |
| WO | 2013/044371 A1 | 4/2013 |

OTHER PUBLICATIONS

Bar et al., "A new approach for design of organic electrochromic devices with inter-digitated electrode structure", Solar Energy Materials & Solar Cells, vol. 93, 2009, pp. 2118-2124.
Bechinger et al., "Photoelectrochromic windows and displays", Letters to Nature, vol. 383, pp. 608-610.
Deb et al., "Stand-alone photovoltaic-powered electrochromic smart window", Electrochimica Acta, vol. 46, 2001, pp. 2125-2130.
Extended European Search Report from European Application No. 10785617.1 dated Jan. 31, 2013.
Gilat et al., "Light-triggered Electrical and Optical Switching Devices", J. Chem. Soc., vol. 18, 1993, pp. 1439-1442.
Gorodetsky, Brian, "The Design of Dual-Mode Photochromic and Electrochromic 1,2-Dithienylcyclopentene Dyes", PhD Dissertation, Simon Fraser University, Ch. 1 and 5, Section 4.4, 2008.
International Preliminary Report on Patentability from International Application No. PCT/CA2010/000849 dated Dec. 12, 2011.
International Preliminary Report on Patentability from International Application No. PCT/CA2011/001378 dated Jun. 18, 2013.
International Search Report and Written Opinion from International Application No. PCT/CA2010/000849 dated Oct. 27, 2010.
International Search Report and Written Opinion from International Application No. PCT/CA2011/001377 dated Apr. 5, 2012.
International Search Report nd Written Opinion from International Application No. PCT/CA2011/001378 dated Apr. 3, 2012.
Notification Concerning Transmittal of International Preliminary Report on Patentability from International Application No. PCT/CA2011/01377 dated Jun. 27, 2013.
Zhang et al., "An UV photochromic memory effect in proton-based WO3 electrochromic devices", Applied Physics Letters, vol. 93, 2008, pp. 203508-1-203508-2.
Coleman et al., "Printed, flexible electrochromic displays ing interdigitated electrodes", Solar Energy Materials & Solar Cells, vol. 56, 1999, pp. 395-418.
Office Action issued in corresponding European Patent Application No. 11 849 064.8, dated Aug. 16, 2016, 7 pages.

* cited by examiner

VARIABLE TRANSMITTANCE OPTICAL FILTER WITH SUBSTANTIALLY CO-PLANAR ELECTRODE SYSTEM

RELATED CASES

This application is a Continuation Application of U.S. patent application Ser. No. 14/932,602, filed Nov. 4, 2015, now U.S. Pat. No. 9,568,799, which is a Continuation of U.S. patent application Ser. No. 13/994,409, filed Jun. 14, 2013, now abandoned, which is a National Stage Application of International Patent Application No. PCT/CA2011/001378, filed Dec. 15, 2011, which claims the benefit of U.S. Provisional Application No. 61/423,536 filed Dec. 15, 2010, which applications are incorporated herein by reference. To the extent appropriate, a claim of priority is made to each of the above disclosed applications.

FIELD OF THE INVENTION

The present invention relates to the field of variable transmittance optical filters, in particular to those comprising an optical filter capable of transitioning from one state of visible light transmittance to another with application of an electric voltage to a substantially co-planar electrode system.

BACKGROUND OF THE INVENTION

Optical filters are widely used to control visible and solar energy. Most notably, optical filters have been used as glazings in window technology (e.g. windows of buildings, vehicles, aircraft, spacecraft, ships or the lie) to control the flow of light and heat into and out of the glazing, for glare reduction and energy load management. Improving the energy efficiency of buildings is a key aspect of reducing energy use and reducing $CO_2$ emissions. Buildings consume about 39% of all energy and 68% of the electricity used in the United States, and are responsible for about 38% of all greenhouse gas (GHG) emissions. Windows are responsible for about 30% of a buildings energy loss. As such, windows with improved technology for reducing heat loss and solar heat gain can offer significant benefits and cost savings.

Optical filters ("tinted windows") may be used in vehicle windows to provide privacy for occupants, prevent glare and/or reduce solar heat gain without sacrificing visibility. Static tints generally cannot be altered, and if further 'darkening' is desired, a blind may be drawn—eliminating any visibility for the occupants. 'Panoramic' sunroofs may be installed to provide visibility to occupants (e.g. for sightseeing—'dome roofs') and provide a feeling of 'being outside', a drawn blind does not accommodate this desire, and for a large roof or dome, may be difficult for a user to manipulate at will.

Optical filters have also found application in ophthalmic devices to control the light impacting the eye. Applications include, for example, prescription and nonprescription glasses, goggles, sunglasses, visors, and safety eyewear.

There are a number of technologies that have been used in optical filter applications for dynamically varying the degree of visible light transmittance, including photochromics, electrochromics, liquid crystals, thermochromics, and suspended particle displays.

Some optical filters used in window applications requiring the application of electrical voltage to vary the degree of visible light transmittance—such devices typically comprise two transparent conductive electrodes on opposing substrates to which the electrical voltage is applied. These transparent conductive electrodes can be formed using a conductive coating such as indium-tin oxide (ITO) on glass or polymeric film. A material that transitions from one state of visible light transmittance to another upon the application of electrical voltage is sandwiched between the two transparent conductive electrodes. For example, electrochromic technology involves applying thin coatings of electrochromic materials to two transparent conductive electrodes and sandwiching an electrolyte material in between. Electrochromic technology typically requires the user to apply external electrical power to darken. Electrochromic technology is used in auto-dimming automobile mirrors (for example, those made by Gentex Corporation of Zeeland Mo.).

Another example of electrochromics is in window applications (Sage Electrochromics Inc. of Faribault, Minn.) that incorporate thin coatings applied to one of the glass layers in a window. Application of electricity with the positive lead connected to one electrode causes the window to darken, and application of electricity with the positive lead connected to the other electrode causes the window to lighten. The electrochromic coating that is applied to the glass involves the use of specialized coating processes such as sputtering and chemical vapor deposition. This often requires a specialized factory or facility requiring the glass to be shipped to one central factory for the coating process to be performed, and then shipped out to wherever they will be used. As such, windows made using electrochromic technology can be quite expensive. This type of window system also employs an electrode system with two conductive transparent electrodes on opposing substrates.

Electrochromics have also been used in ophthalmic devices. For example, ChromoGenics of Uppsala, Sweden makes an "electrochromic foil" for use in motorcycle helmet visors and other products by making a multi-layer electrochromic device between two plastic films. Relatively low DC voltages are used for switching the electrochromics from one state to another but power is typically required to maintain the electrochromic device in the dark state. These electrochromic foils also utilize an electrode system with two conductive transparent electrodes on opposing substrates.

Patterning of ITO (indium tin oxide) has been used to prepare for liquid crystal displays and touch panels. The objective of patterning the ITO in these cases is to create an array of pixels such that each pixel can be uniquely addressed and either turned on or off or a touch detected, depending on the application.

Interdigitated electrodes have been described in the design of organic electrochromic devices with three-electrode dynamic operation for display technology (Galit Bar et al., "A new approach for design of organic electrochromic devices with interdigitated electrode structure," Solar Energy Materials & Solar Cells (2009) 93:2118-2124)).

U.S. Pat. No. 7,323,634 describes a method of forming an electronic circuit component using the technique of drop on demand printing to deposit droplets of deposition material, the method comprising depositing a plurality of droplets on a surface to form a patterned electronic device comprising multiple discrete portions.

United States Patent Publication No. 20070128905 describes transparent electrical conductors comprising regions of high transparency and regions of lower transparency, but higher conductivity. This allows electrical connection through the conductor, while retaining its transparency for such applications as hand-held device display screens or transparent antennas, for example.

United States Patent Publication No. 20070153355 describes an electrochromic film and demonstrates the electrochromic effect of a single substrate film by applying electronic current to induce a reversible oxidation-reduction reaction of an organic electrochromic layer. The electrochromic film can attach to a surface of an object with the use of an adhesive layer.

U.S. Pat. Nos. 6,597,489 and 6,606,184 describe an electrode device for an electrochromic device, where the electrodes are disposed on a substrate in a substantially coplanar relation. An electrochromic medium comprising a cathodic and an anodic species, at a ratio within the electrochromic medium in relation to the surface areas of the positive and negative electrodes is described.

SUMMARY OF THE INVENTION

The present invention relates to variable transmittance optical filters, more particularly those comprising a co-planar, or substantially co-planar electrode, and capable of transitioning from a first transmittance state to a second transmittance state with application of an electric voltage.

In accordance with one aspect of the invention, there is provide a variable transmittance optical filter comprising: a) a first layer comprising a first substantially transparent substrate with a substantially co-planar (SC) electrode system disposed thereon, the SC electrode system made of transparent electrically conductive material and comprising at least one pair of electrically separate electrodes arranged in a substantially co-planar manner on the first substantially transparent substrate, each pair of electrically separate electrodes comprising a first electrode and a second electrode, b) a second layer proximate to the first layer and comprising a transition material that darkens in response to a nonelectrical stimulus and lightens in response to application of an electric voltage; and c) an electrical connection system for electrically connecting the SC electrode system to a source of electric voltage.

In accordance with another aspect of the invention, there is provided a variable transmittance optical filter comprising: a) a first layer comprising a first substantially transparent substrate with a substantially co-planar (SC) electrode system disposed thereon, the SC electrode system made of transparent electrically conductive material and comprising at least one pair of electrically separate electrodes arranged in a substantially co-planar manner on the first substantially transparent substrate, each pair of electrically separate electrodes comprising a first electrode and a second electrode, b) a second layer proximate to the first layer and comprising a transition material that is capable of dynamically varying the degree of visible light transmittance on application of an electric voltage; and c) an electrical connection system for electrically connecting the SC electrode system to a source of electric voltage, wherein after a positive voltage is applied to the first electrode and a negative voltage is applied to the second electrode, the polarity of the voltage applied to the first electrode and the second electrode is alternately reversed one or more times to transition the transition a first state of visible light transmittance to a second state of visible light transmittance.

In accordance with another aspect of the invention, there is provided a variable transmittance optical filter comprising: a) a first layer comprising a first substantially transparent substrate with a substantially co-planar (SC) electrode system disposed thereon, the SC electrode system made of transparent electrically conductive material and comprising two or more pairs of electrically separate electrodes arranged in a substantially co-planar manner on the first substantially transparent substrate, each pair of electrically separate electrodes comprising a first electrode and a second electrode, b) a second layer proximate to the first layer and comprising a transition material that is capable of dynamically varying the degree of visible light transmittance on application of an electric voltage; and c) an electrical connection system for electrically connecting the SC electrode system to a source of electric voltage.

In accordance with another aspect of the invention, there is provided a method of preparing a variable transmittance optical filter comprising the steps of: providing a first layer comprising a first substantially transparent substrate with a substantially transparent, electrically conductive material disposed thereon; etching into the electrically conductive material a substantially co-planar (SC) electrode system, the SC electrode system comprising at least one pair of electrically separate electrodes arranged in a substantially co-planar manner, each pair of electrically separate electrodes comprising a first electrode and a second electrode; disposing a second layer proximate to the SC electrode system, the second layer comprising a transition material that is capable of dynamically varying the degree of visible light transmittance on application of an electric voltage; and providing an electrical connection system electrically connecting the SC electrode system to a source of electric voltage.

In accordance with another aspect of the invention, there is provided a method of preparing a variable transmittance optical filter comprising the steps of: providing a first layer comprising a first substantially transparent substrate; printing onto the first substrate a substantially co-planar (SC) electrode system using a conductive ink, the SC electrode system comprising at least one pair of electrically separate electrodes arranged in a substantially co-planar manner, each pair of electrically separate electrodes comprising a first electrode and a second electrode; disposing a second layer proximate to the SC electrode system, the second layer comprising a transition material that is capable of dynamically varying the degree of visible light transmittance on application of an electric voltage; and providing an electrical connection system electrically connecting the SC electrode system to a source of electric voltage.

In accordance with another aspect of the invention, there is provided a method of transitioning a transition material from a dark state to a faded state comprising the steps of: applying a positive voltage to a first electrode and a negative voltage to a second electrode; reversing the polarity of the voltage, thereby applying a negative voltage to the first electrode and a positive voltage to the second electrode. In various aspects, the polarity of the voltage may be reversed once, or more than once.

In various embodiments, the voltage applied to the first and second electrodes is from about 0.5 to about 3.0 V, or from about 1.2V to about 2.5 V, or from about 1.8V to about 2.2 V, or any amount or range therebetween.

In various aspects, the variable transmittance optical filter further comprises a third layer comprising a second substantially transparent substrate.

In various aspects, the first and second electrodes may each comprise finger-like structures, and may be interdigitated. The finger-like structures may be substantially the same length. The fingerlike structures may form a linear or curvilinear unit. The fingerlike structures may have an interdigit spacing of from about 10 µm to about 1 mm or any amount or range therebetween.

In various aspects, the width of the fingerlike structures of the first electrode may be the same, or substantially the same, as the width of the fingerlike structures of the second electrode. The surface area of the first electrode may be substantially the same as the surface area of the second electrode.

In various aspects, the width of the fingerlike structures of the first electrode may be greater than the width of the fingerlike structures of the second electrode. The surface area of the first electrode may be greater than the surface area of the second electrode. The ratio of the width of the first electrode to the second electrode is from about 2:1 to about 100:1 or any amount or range therebetween. The first electrode and the second electrode may have a relative area of about 2:1 to about 1000:1 or any amount or range therebetween.

In various aspects the first electrode may be an anode, and the second electrode a cathode. In other aspects, the first electrode may be a cathode and the second electrode an anode.

In various aspects, the transition material may comprise a hybrid photochromic/electrochromic (hybrid P/E) compound. The hybrid P/E compound may be organic. The hybrid P/E compound may be an anodic species. The hybrid P/E compound may be selected from the group comprising diarylethenes, dithienylcyclopentenes and fulgides. The non-electrical stimulus may be light. The light may comprise wavelengths of about 350 to about 420 nm, or of about 365 to about 420 nm, or of about 375 to about 420 nm, or of about 375 to about 420 nm, or of about 380 to about 420 nm, or of about 385 nm to about 420 nm, or any amount or range therebetween.

In various aspects the first substantially transparent substrate and the second substantially transparent substrate are independently rigid or flexible, and may each independently be glass or a thermoplastic polymer.

In various aspects, the variable transmittance optical filters may be a film, and may comprise part of an architectural window, a vehicle (e.g. automotive) window, an opthalmic device, or the like.

This summary of the invention does not necessarily describe all features of the invention. Other aspects, features and advantages of the present invention will become apparent to those of ordinary skill in the art upon review of the following description of specific embodiments of the invention.

BRIEF DESCRIPTION OF THE DRAWINGS

These and other features of the invention will become more apparent in the following detailed description in which reference is made to the appended drawings.

DESCRIPTION OF THE INVENTION

Figure 1:
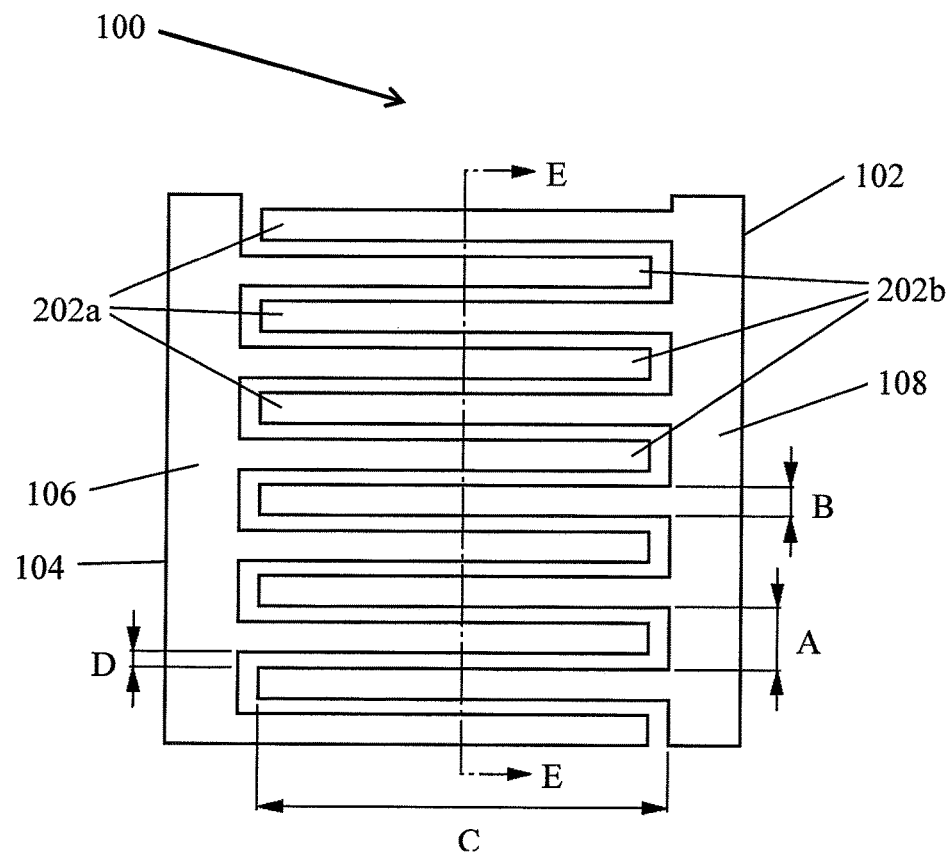
FIG. 1 is a schematic top view of a symmetric interdigitated electrode structure, according to some embodiments of the invention.

The present invention relates, in part, to a variable transmittance optical filter ("optical filter", "filter" or "VTOF") that is capable of transitioning from one state of visible light transmittance to another with the application of an electric voltage. The variable transmittance optical filter comprises a first layer comprising a substantially transparent substrate (a "substrate" or a "first substrate") with a substantially coplanar (SC) electrode system disposed thereon, a second layer proximate to, for example in contact with, the first layer and comprising a transition material that is capable of dynamically varying the degree of visible light transmittance (VLT), and an electrical connection system for electrically connecting the SC electrode system to a source of electric voltage. The variable transmittance optical filter may optionally comprise a third layer having a substantially transparent substrate (a "second substrate").

The SC electrode system is made of transparent electrically conductive material that can be adhered to or etched in a layer on the substantially transparent substrate. The SC electrode system comprises at least one pair of electrically separate electrodes arranged in a substantially co-planar manner on the substantially transparent substrate. Each pair of electrodes comprises a first electrode and a second electrode (collectively, "electrodes"). In operation, a positive potential may be applied to either the first or the second electrode, and a negative potential applied to the remaining electrode. An electrode to which a positive potential is applied may be referred to herein as an anode; an electrode to which a negative potential is applied may be referred to herein as a cathode. In some embodiments, the SC electrode system comprises more than one pair of electrically separate electrodes arranged in a substantially co-planar manner on the substantially transparent substrate. In some embodiments, the application of voltage can be reversed in polarity one or more times in order to facilitate transition of the transition material from one state of visible light transmittance to another. In some embodiments, the first electrode is an anode and the second electrode is a cathode; in some embodiments, the first electrode is a cathode and the second electrode is an anode; in some embodiments, reversal of polarity may apply an opposite charge to the first or the second, or the first and the second electrode.

In embodiments of the present invention, two electrodes may be substantially co-planar, in that they both reside in a first layer of material or space, while the transition material generally resides in a second, adjacent layer of space or material. The layers may be flat, or may comprise one or more curves. One or more, but not necessarily all, two-dimensional cross sections taken through the first layer contains portions of both the electrodes—see, for example, FIGS. 1 and 2. As an example, two electrodes may be deemed to be substantially co-planar if both electrodes contact, or nearly contact, the same surface of the transition material. The design of the electrodes of the SC electrode system can be varied with respect to the width or surface area of the electrodes, the separation distance between the electrodes, the level of interdigitation, and characteristics of the applied voltage, such as level, duration, and polarity, in order to tailor the structure and function of the optical filter to the specific application where a variable transmittance optical filter with SC electrode system may be used. As the variable transmittance optical filter with SC electrode system comprises only one layer with a transparent conductive substrate, optical filters according to various embodiments of the invention are of simplified design, may require fewer components and may be lower in cost to manufacture.

The variable transmittance optical filter with an SC electrode system can employ transition materials known in the art for transitioning from one state of visible light transmittance to another with the application of power (a voltage) to the electrodes. Examples include, but are not limited to, for example, electrochromic, liquid crystal, or suspended particle technology to enable transition from one state of visible light transmittance to another upon application of an electric voltage. In some embodiments, a hybrid photochromic/electrochromic transition material exemplified herein, can be used in the variable transmittance optical filter.

The variable transmittance optical filter can be used in devices where a transition from one state of visible light transmittance to another upon application of the electric voltage is useful. Examples of such devices include, for example, an optical film, an architectural window, automotive window, ophthalmic device, displays, signage, or the like.

The term "visible light" (VIS) as used herein, refers to the band of electro-magnetic radiation with a wavelength from about 400 nm to about 750 nm. The term "ultraviolet (UV) light" as used herein, refers to electromagnetic radiation with a wavelength shorter than that of visible light, or from about 10 nm to about 400 nm. In some embodiments, sub-ranges of ultraviolet light may be used, for example from about 100 to about 400 nm, or from about 200 to about 400 nm, or from about 300 to about 400 nm, or from about 350 to about 400 nm. The term "infrared radiation (IR)" as used herein, refers to electromagnetic radiation with a wavelength from about 750 nm to about 50,000 nm. Its wavelength is longer than that of visible light. Light may also be described with reference to colour or range of wavelength.

A "light source" is a source of VIS, UV and/or infrared light (IR). A light source may also provide full spectrum light, including one or more of VIS, UV and IR light, or light of wavelengths within a VIS, UV or IR range. Light sources may include natural or simulated sunlight (direct or indirect), or light from a selected wavelength or range of wavelengths. The selected wavelength or range of wavelengths may be selected by the nature of the light source itself (e.g. a lamp that produces light in a particular range such as a UV lamp, or may be selected through use of a cutoff filter, designed to eliminate light above or below a cutoff wavelength, or between two cutoff wavelengths. In some embodiments of the invention, the light source may be configured to provide light above or below a predetermined wavelength, or may provide light within a predetermined range. A device or apparatus according to some embodiments of the invention may comprise a light source.

Devices according to various embodiments of the invention may be described with reference to clarity, visible light transmittance, switching speed, durability, photostability, contrast ratio, state of light transmittance (e.g. dark state or light state) to further define the device, or aspects of the device; some values or characteristics of such descriptors may be applicable to some or all devices, but only exemplified in one type of device; alternately, some values or characteristics of such descriptors may be applicable to only a few types of devices.

"Visible light transmittance (VLT)" refers to the quantity and/or wavelength range of visible light that is transmitted or passes through a substance or product. VLT may be expressed with reference to a change in light transmission and/or a particular type of light or wavelength of light (e.g. from about 10% visible light transmission (VLT) to about 90% VLT, or the like). A product with a higher VLT transmits more visible light. VLT is expressed as a number between 0 and 1, or as a percentage. VLT may alternately be expressed as absorbance, and may optionally include reference to one or more wavelengths that are absorbed. According to various embodiments of the invention, a material may have a contrast ratio of at least about 2, at least about 3, at least about 4, at least about 5, at least about 6, or any amount or range therebetween. It will be appreciated by those skilled in the art that other configurations of % VLT in light and dark states, and contrast ratios thereof, may be possible with other compounds, formulations or the like. According to some embodiments, an optical filter may be selected, or configured to have in the dark state, a VLT of less than 80%, or less than 70%, or less than 60%, or less than 50%, or less than 40%, or less than 30%, or less than 20% or less than 10%, or any amount or range therebetween. According to some embodiments, an optical filter may be selected, or configured to have in the light state, a VLT of greater than 80%, or greater than 70%, or greater than 60%, or greater than 50%, or greater than 40%, or greater than 30%, or greater than 20% or greater than 10%, or any amount or range therebetween. Inclusion of a colourant or coloured film in the optical filter may additively reduce the VLT of the optical filter, in combination with the transition material. In some embodiments, the VLT of an optical filter in the dark state or the light state may independently be 1, 2, 3, 4, 5, 6, 7, 8, 9, 10, 12, 14, 16, 18, 20, 25, 30, 35, 40, 45, 50, 55, 60, 65, 70, 75, 80, 85, 90 or 95%, or any amount or range therebetween, with the proviso that the dark state of an optical filter has lesser VLT than the light state of the same optical filter.

The term "state of visible light transmittance" as used herein, refers to states such as a dark state, or a light state, or transition states in between, for example. A transition material may darken (e.g. reach a 'dark state') when exposed to light (e.g. ultraviolet light) from a light source, or when a voltage is applied, and may lighten ("fade", "electrofade", "bleach", "electrobleach", achieve a "light state") when exposed to an electric charge, or when exposed to visible light of a selected range. Such a transition material may be alternately described as an auto-darkening material. In some embodiments, the transition material may fade upon exposure to selected wavelengths of visible (VIS) light ("photofade", "photobleach"), without sacrifice of the ability to be electrofaded when restored to a darkened state. This term also refers to states such as opaque, clear, translucent, or transparent. For example, the term "dark state" can refer to a state in which there is a low to no transmittance of visible light. The term "light state" can refer to a state in which there is a high degree of transmittance of visible light. Dark state and light state may be described relative to each other.

The contrast ratio is a ratio of the VLT of a compound or material in the dark state and the light state. For example, a material may allow transmission of about 10% of the visible light (10% VLT) in a dark state, and about 60% of the visible light (60% VLT) in a faded state, providing a contrast ratio of about 6 (e.g. 6:1). According to various embodiments of the invention, a material may have a contrast ratio of at least about 2, or 3, or 4, or 5, or 6, or 7, or, or 9, or 10, or 11, or 12, or any amount or range therebetween. It will be appreciated by those skilled in the art that other configurations of % VLT in light and dark states, and contrast ratios thereof, may be possible with other compounds, formulations or the like.

The term "mil" as used herein, refers to the unit of length for $\frac{1}{1000}$ of an inch (0.001). One (1) mil is about 25 microns; such dimensions may be used to describe the thickness of an optical filter or components of an optical filter, according to some embodiments of the invention.

The term "ophthalmic device" or "ophthalmics" as used herein refers to a device placed in front of the eye to control the light impacting the eye. The term encompasses, for example, glasses (prescription and non-prescription), goggles, sunglasses, and visors or the like.

The term "about" refers to a +/−20% variation from the nominal value. It is to be understood that such a variation is always included in any given value provided herein, whether or not it is specifically referred to.

Variable Transmittance Optical Filter

The invention provides, in part a variable transmittance optical filter comprising a first layer comprising a substantially transparent substrate with a substantially co-planar (SC) electrode system disposed thereon, a second layer proximate to (e.g. in contact with) the first layer, comprising a transition material that is capable of dynamically varying the degree of visible light transmittance, and an electrical connection system for electrically connecting the SC electrode system to a source of electric voltage.

1. First Layer and Optional Third Layer

The first layer of the variable transmittance optical filter comprises a substantially transparent substrate with a SC electrode system disposed thereon. The variable transmittance optical filter may optionally comprise a third layer that comprises a substantially transparent substrate, without an SC electrode system. Substantially transparent substrates suitable for use in the variable transmittance optical filters according to the invention are described below.

In some embodiments, the SC electrode system may be provided without being disposed on a substantially transparent substrate, if sufficient structural integrity is provided by another layer or means. For example, the SC electrode system may comprise two or more separate electrode components which may be disposed on the second layer comprising the transition material, provided the second layer has sufficient structural integrity. For example, the electrode components may be applied as decals or stickers to the second layer, or may otherwise be disposed on the second layer via lithography, printing or other suitable methods. However, one or more substantially transparent substrates may be desirable in embodiments of the present invention for providing rigid or flexible structural integrity, physical protection, optical filtering protection, and the like.

1.1 Substantially Transparent Substrates

The substantially transparent substrate of the optical filter of the present invention provides sufficient structural integrity to support the SC electrode system and the transition material. Rigid or flexible substrates can be used as applicable to a broad range of applications as discussed below. For example, variable transmittance optical filters of the invention that are made with a rigid substrate can operate alone in a particular application, such as a window application. Alternatively, variable transmittance optical filters of the invention that are made with a flexible substrate can operate as a variable transmittance optical film that can be laminated, for example, on the selected application.

Examples of suitable materials that can be used as a substrate in the present invention include, but are not limited to, glass and thermoplastic polymers. Suitable thermoplastic polymers include polyesters (PE), polycarbonates, polyamides, polyurethanes, polyacrylonitriles, polyacrylacids, (e.g. poly(methacrylic acid), including polyethylene terephthalate (PET), polyolefins (PO) or copolymers or heteropolymers of any one or more of the above, or copolymers or blends of any one or more of the above with poly(siloxane)s, poly(phosphazenes)s, or latex. Examples of polyesters include homopolymers or copolymers of aliphatic, semi-aromatic or aromatic monomeric units, for example polycondensed 4-hydroxybenzoic acid and 6-hydroxynapthalene-2-carboxylic acid (VECTRAN™), polyethylene napthalate (PEN), polytrimethylene terephthalate (PTT), polybutylene terephthalate (PBT), polyethylene terephthalate (PET), polyhydroxyalkanoate (PHA), polyethylene adipate (PEA), polycaprolactone (PCL) polylactic acid (PLA), polyglycolic acid (PGA) or the like. Examples of polycarbonates include bisphenol A polycarbonate or the like. Other thermoplastic polymers include polyethene (PE), polypropylene (PP) and the like. In one embodiment of the invention, the substrate material is glass. In one embodiment of the invention, the substrate material is PET. In one embodiment of the invention, the substrate is heat-stabilized PET. Suitable glass includes float glass, tempered glass, laminated glass, tinted glass, mirrored glass, reinforced glass, safety glass, bullet-resistant glass, "one-way" bullet-resistance glass, Other suitable substrate materials include ceramic spinel or aluminum oxynitride. For an optical filter or a device comprising two or more substrates, the substrates may be the same material, or different. The material comprising a substrate may have UV, IR or VIS light blocking characteristics.

In a further embodiment of the invention, at least one of the substrates incorporates a UV blocker in, or on, the substrate. In embodiments of the invention, a UV blocker (e.g. a UV blocking layer or film applied to a substrate, or combined with material of a substrate) is provided which blocks or reflects a portion of the incident UV light, but still allow transmission of a portion of the incident light to allow for photochromic transitioning of the transition material. In some embodiments, the material comprising the substrate, and/or an adhesive for applying the variable optical filter to a surface, may have UV blocking activity. The UV blocker can be a polymer film comprising an organic UV absorbing compound (for example xanilides, benzophenones, benzotriazoles hydroxyphenyltriazines or the like), or an inorganic UV absorbing material (for example nano zinc particles), or a UV reflecting compound (for example nano-titanium or nano zinc), or a combination thereof. Examples of UV blocking films, materials or agents that may be combined with a substrate (e.g. when it is mixed, molded, cast or cross-linked), or included in a transition material are provided herein. A UV blocker may be deposited by any suitable method, for example chemical vapor deposition, physical vapor deposition, (e.g. sputtering, electron beam evaporation, and ion plating), plasma spray techniques, sol-gel processes or the like. In some embodiments, an adhesive employed to affix an optical filter in the form of a film to a pane of a window or a lens may be, or comprise, a UV blocker. Blocking a portion of the incident UV light may increase the durability of the optical filter.

One skilled in the art will appreciate that the thickness of the selected substrate may be configured so as to allow for sufficient structural integrity to support the transition material while providing sufficient rigidity or flexibility for the particular application of use, as well as sufficient transparency. Determination of an appropriate material and thickness is considered to be within the ordinary skills of a worker in the art. In one embodiment of the invention, the substrate has a thickness of between about 0.012 mm and about 10 mm. The substrate may be rigid or flexible. In one embodiment, the substrate material is rigid and has a thickness of between about 0.5 mm and 10 mm, or between about 1 mm and 5 mm, or a thickness of about 0.5, 1, 2, 3, 4, 5, 6, 7, 8, 9 or 10 mm, or any amount or range therebetween. In one embodiment, the substrate material is flexible and has a thickness of between about 0.024 mm and about 0.6 mm, or between about 0.051 mm (about 2 mil) to about 0.178 mm (about 7 mil), or a thickness of about 0.2, 0.3, 0.4, 0.5, 0.6, 0.7, 0.8, 0.9 or 1 mm, or any amount or range therebetween.

Combinations of substrate materials and thicknesses are also contemplated for use in the variable transmittance optical filter of the present invention. In some embodiments, a variable transmittance optical filter of the present invention comprises a first layer with a UV blocker material. In some embodiments, a variable transmittance optical filter of the present invention comprises a first layer with a substrate that is rigid and a third layer with a substrate that is flexible. In a further embodiment, a variable transmittance optical filter of the present invention comprises a first layer with a substrate having a thickness of 5 mil and a third layer having a substrate having a thickness of 2 mil.

The substrates can optionally include additives such as base colour tints to provide a darker overall range or colour to the optical filter, and/or UV blocking compounds to block certain wavelengths of electromagnetic radiation. In some embodiments, the optical filter of the present invention comprises a first layer and/or a third layer with a substrate having a barrier coating to block moisture. In some embodiments, the substrate of the first and/or third layer has an anti-reflective coating. In some embodiments, the substrate of the first and/or third layer has a scratch resistant coating. In some embodiments, the first and/or third layer has a substrate having a pressure-sensitive adhesive coating for laminating the variable transmittance optical filter onto glass. In some embodiments, an air gap may be provided between the third layer and an adjacent layer, for example to facilitate thermal insulation.

1.2. Substantially Co-Planar (SC) Electrode System

The SC electrode system is made of transparent electrically conductive material that can be adhered to or etched in a layer on the substantially transparent substrate. The SC electrode system comprises at least one pair of electrically separate electrodes arranged in a substantially co-planar manner on the substantially transparent substrate. A potential difference may be applied across the pair of electrodes. For example, each pair of electrodes may comprise one electrode to which a positive potential is applied (anode) and one electrode to which a negative potential is applied (cathode). In some embodiments, the anode and cathode may be switchably reversed by reversing the polarity on the pair of electrodes so that the anode becomes the cathode and the cathode becomes the anode.

The SC electrode system may comprise multiple pairs of electrodes that can be controlled as a single unit, in groups, or individually in order to provide fine tuning of the transition of the variable transmittance optical filter from one state of visible light transmittance to another. SC electrode systems with multiple electrode pairs may thus be useful in embodiments where the transition from one state of visible light transmittance to another in some areas of the variable transmittance optical filter is to be controlled differently from that in other areas of the variable transmittance optical filter.

As described herein, in some embodiments, the application of voltage to the SC electrode pairs can be reversed in polarity one or more times in order to facilitate transition of the transition material from one state of visible light transmittance to another.

1.2.1 Transparent Electrically Conductive Material

The variable transmittance optical filter comprises a substantially co-planar electrode system having electrodes made of transparent electrically conductive material that can be adhered in a layer to, or otherwise disposed on, the substrate. This material is typically an inorganic or intrinsically conducting organic material. Suitable materials for the transparent conductive layers are well-known to those skilled in the art and include, for example, metal oxides, carbon nanotubes, and fine wire meshes. Exemplary conductive materials include layers of doped indium tin oxide, doped tin oxide, doped zinc oxide, antimony tin oxide, polyaniline, graphene, PEDOT (poly(3,4-ethylenedioxythiophene)), PEDOT:PSS (poly(3,4-ethylenedioxythiophene) poly(styrenesulfonate)), and polypyrrole as well as thin, substantially transparent metallic layers such as gold, silver, aluminum, and nickel alloy.

In embodiments of the present invention, the electrodes of the SC electrode system may be formed from a transparent conductive material generally exhibiting a predetermined sheet resistance. As would be readily understood by a worker skilled in the art, increased sheet resistance in some transparent conducting materials may correspond with increased VLT. In some embodiments of the invention, the variable transmittance optical filter of the invention comprises SC electrode system formed from a transparent conductive material having a sheet resistance of up to about 100 Ohms/square, or up to about 1000 Ohms/square, or up to about 100,000 Ohms/square or up to about 1,000,000 Ohms/square, or any amount or range therebetween. In some embodiments of the invention, the transparent conductive material may have a sheet resistance from about 10 Ohms/square to about 1000 Ohms/square; or from about 20 Ohms/square to about 500 Ohms/square; or from about 100 Ohms/square to about 1,000 Ohms/square; or from about 1,000 Ohms/square to about 10,000 Ohms/square; or from about 10,000 Ohms/square to about 1,000,000 Ohms/square; or from about 1,000,000 Ohms/square to about 5,000,000 Ohms/square; or from about 5,000,000 to about 10,000,000 Ohms/square; or any amount or range therebetween.

As will be understood by one of skill in the art, the first layer comprising a substantially transparent substrate with a transparent electrically conductive coating, may be selected to have a high degree of visible light transmittance (VLT), or a low degree of VLT, depending on the intended use of the optical filter. For example, the first substrate with conductive layer may have a VLT of at least 50%, at least 60%, at least 70%, at least 80%, at least 90%, or at least 95%, or any amount or range therebetween. For an embodiment where the optical filter is desired to block at least 90%, or substantially all light (e.g. an opaque, or substantially opaque optical filter when in a dark state), the first substrate with conductive layer may be selected, or configured for a VLT of less than 50%, or less than 40%, or less than 30%, or less than 20% or less than 10%, or any amount or range therebetween.

1.2.2 SC Electrode System Pattern

The SC electrode system comprises at least one pair of electrically separate electrodes (first and second electrodes) arranged in a substantially co-planar manner on the substantially transparent substrate. A positive and negative potential may be applied to these electrodes, or the electrode system, as described herein. As described herein, it is contemplated that an electrode acting as an anode may be switched such that it acts as a cathode, by reversing the polarity of the voltage applied, and, as described herein, it is contemplated that an electrode acting as a cathode may be switched such that it acts as a anode, by reversing the polarity of the voltage applied.

In some embodiments, the SC electrode system comprises a plurality (more than one) pairs of electrodes located in different regions of the first layer of the variable transmittance optical filter. This may allow individual control of different regions of the variable transmittance optical filter, as noted above. In some embodiments, the plurality of pairs of electrodes may include from about 2 to about 10000 pairs of electrodes, or more, or any amount or range therebetween, for example, 2, 5, 50, 100, 500, 1000, 2000, 5000, 10000 or any amount or range therebetween.

In some embodiments, the SC electrode system is designed in an interdigitated pattern whereby the electrodes of each pair of electrodes are arranged such that the anode and cathode of each pair of electrodes mesh, interlace, alternate, interweave, or are intertwined together, but remain electrically separated. Electrical contact between first and second electrodes is provided by the transition material, such as that described herein. In some embodiments, the SC electrode system is designed such that each electrode of the pair of electrodes is proximate to the other over a substantially large portion of the first layer. In some embodiments where the at least one pair of electrodes is formed in an interdigitated pattern, this may facilitate substantial uniform proximity of the electrodes over a substantial portion of the second layer, thereby facilitating substantially uniform transitioning of the transition material from one state of visible light transmittance to another.

Figure 2:
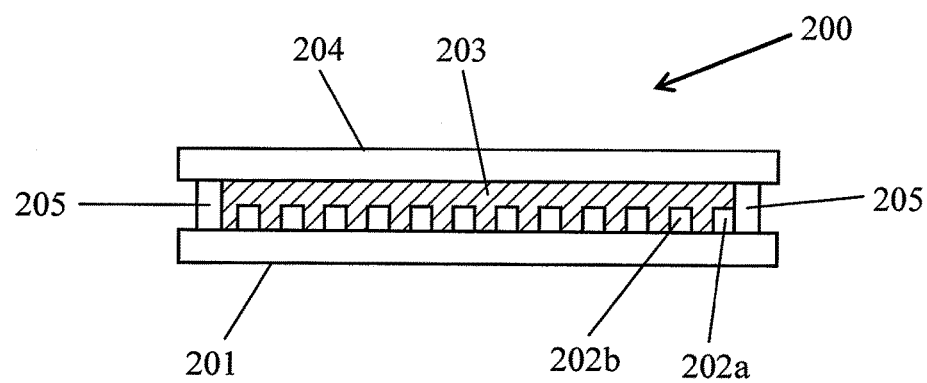
FIG. 2 is a cross sectional schematic diagram along line E-E of the variable transmittance optical filter with SC electrode system of FIG. 1, according to some embodiments of the invention.

In some embodiments, the pattern of the electrodes is such that each electrode comprises fingers or finger-like structures and the fingers or finger-like structures of the anode are interdigitated with the fingers or finger-like structures of the cathode. An illustrative example of an interdigitated electrode pattern is shown in FIGS. 1 and 2. Referring to FIG. 1, an embodiment of a SC electrode system is shown generally at 100. The electrode system comprises a first electrode 102 and second electrode 104, each comprising a plurality of digits 202*a* and 202*b*. In the embodiment shown, the electrodes each comprise a bus bar portion 106, 108. Digit spacing A, digit width B, digit length C and interdigit spacing D are indicated.

FIG. 2 illustrates a cross section along E-E of a variable transmittance optical filter comprising the SC electrode system of FIG. 1, shown generally at 200. The variable transmittance optical filter 200 comprises a first substantially transparent substrate 201 having first 202*a* and second 202*b* interdigitated electrodes disposed thereon. The transition material 203 of the second layer (schematically illustrated, actual proportion of electrode dimension and/or second layer and/or other elements of the optical may vary) is disposed on the electrodes. In the embodiment illustrated, an optional, substantially transparent substrate 204 is included, in contact with the second layer. In some embodiments, seals 205 may be required to keep the transition material sandwiched between the first and third layers as well as to bond the two substantially transparent substrates together. In some embodiments, the transition material 203, may have adhesive functionality and/or comprise an adhesive component and maintain the bond of the first layer and third layer to the transition material of the second layer; in such an embodiment, seals may not be needed. In some embodiments, spacer elements can be incorporated between the substrates in order to maintain a constant distance between them. The spacer elements can be attached to the substrate or the spacer elements can be freely distributed in the transition material.

Figure 3:
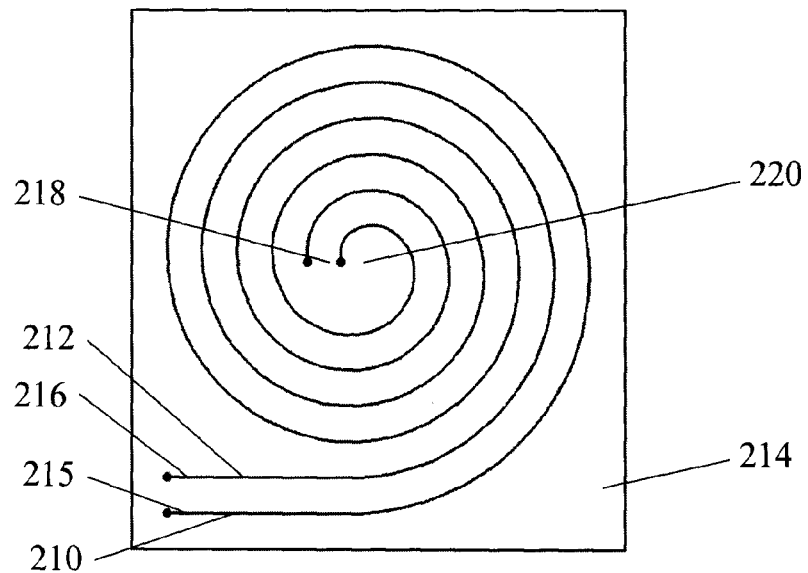
FIG. 3 is a schematic of an interdigitated "jelly roll" electrode pattern, according to some embodiments of the invention.

In other embodiments, the pattern of the electrodes is such that the anode and cathode finger-like structures are aligned to form a linear or curvilinear unit, which can then be arranged in various ways, such as, for example, in rectangular, square, or triangular patterns, or in waves, swirls, or in a "jelly roll" pattern. An example of a "jelly roll" type of interdigitated electrode system design is shown in FIG. 3. First electrode 210 and second electrode 212 describe a coiled configuration on the first substrate 214. Leads (not shown) may connect contact points 215 and/or 218 of the first electrode, and/or contact points 216, 220 of the second electrode to an electrical system to provide a voltage to the electrodes. Combinations of both the finger-like structures and swirl patterns are also contemplated, as are other interdigitated shapes and patterns, exemplified in FIGS. 3-7.

In some embodiments, an electrode may comprise a branched or unbranched structure, or a combination thereof. As an example of a branched structure, one or more conductive protrusions or fingers may branch off from a common bus bar. Branched structures may further comprise plural hierarchical levels of branching, for example a conductive protrusion may itself be a bus bar with protrusions extending therefrom, providing a configuration having primary, secondary, etc. bus bars and/or primary secondary, etc. digits. As an example of an unbranched structure, an electrode may comprise a straight, meandering, "zig-zag" or spiral-shaped conductor. The longest electrical path in a branched structure may generally be shorter than that of a comparable unbranched structure, hence end-to end electrical resistances exhibited by a branched structure may be less than in a comparable unbranched structure.

Other configurations of electrodes include circumferential layout (e.g. FIG. 9), a serpentine layout or the like, as may be appreciated by those skilled in the art.

As described above, in some embodiments of the variable transmittance optical filter, the SC electrode system comprises electrodes with one or more than one "fingers", or finger-like structures, or from about 1 to thousands of fingers or finger-like structures, or any quantity or range therebetween, for example at least 2, 10, 100, 100, 10,000, 100,000, or more fingers or finger-like structures. Fingers or finger-like structures may be provided in a single group, in plural groups, and/or on one or more hierarchical levels.

Figure 5:
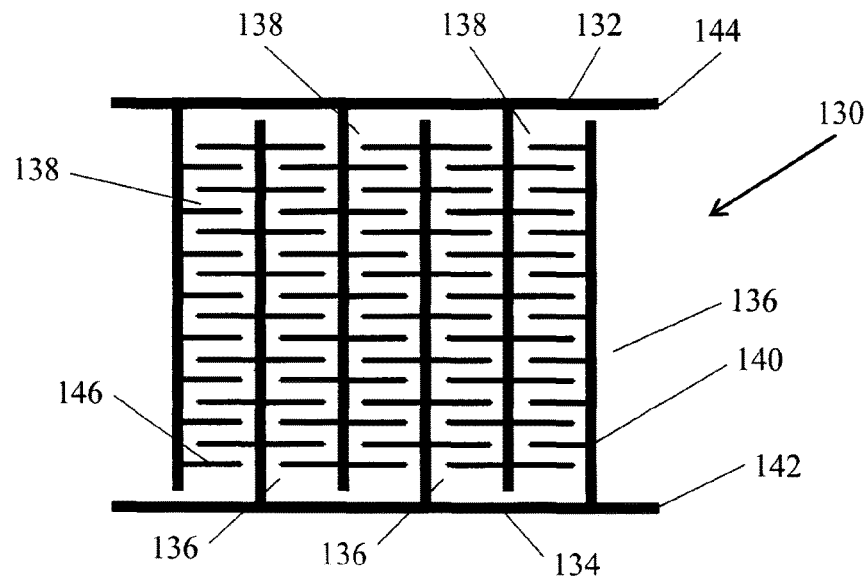
FIG. 5 is a schematic diagram showing a multi-level interdigitated pattern that can be used according to some embodiments of the invention.

The SC electrode system can also be designed to have multiple levels or hierarchies of interdigitation. FIGS. 5-7 and 9 depict exemplary designs for the SC electrode system, comprising multiple levels or hierarchies of interdigitation based on the finger-like structures and swirl patterns described above. Interdigitation may be multilevel or hierarchical in that an interdigitated electrode feature may itself comprise smaller interdigitated features, much like, but not limited to, a finite-level approximation to a fractal geometric structure. Referring to FIG. 5, a multi-level interdigitated SC electrode system is shown generally at 130. First electrode 132 and second electrode 134 each comprise a primary bus bar 142, 144. Extending from each of the primary bus bars of the first and second electrodes are a plurality of secondary bus bars (primary digits) 136, 138, forming a primary level of interdigitation. Each of the primary digits has a plurality of secondary digits 140, 146 extending therefrom, forming a secondary level of interdigitation. Leads (not shown) may connect the first and second electrodes to an electrical system to provide a voltage to the electrodes.

Figure 6:
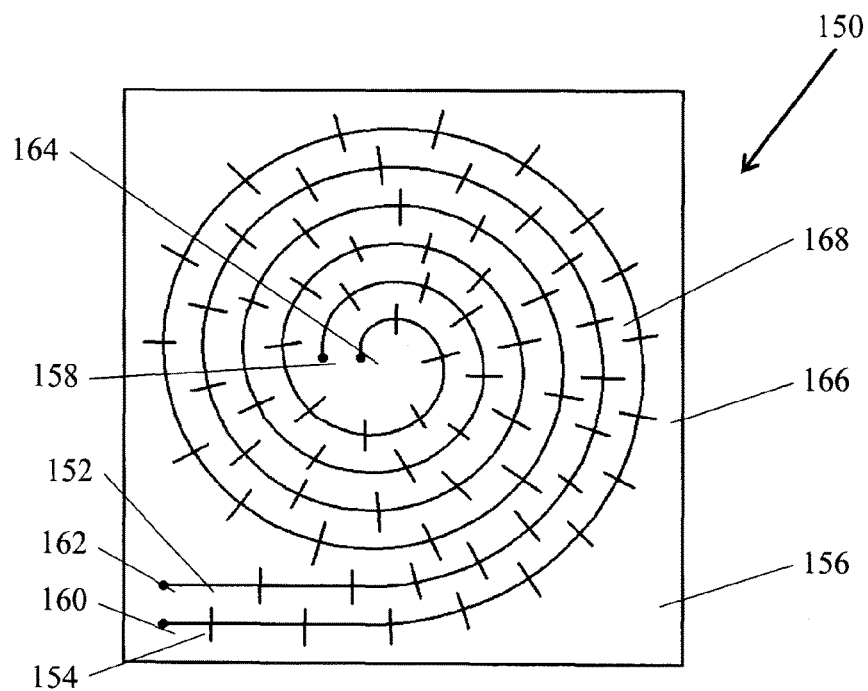
FIG. 6 illustrates a schematic diagram showing an interdigitated electrode in a "jelly roll" pattern, combined with straight finger-like structures, according to some embodiments of the invention.
Figure 7:
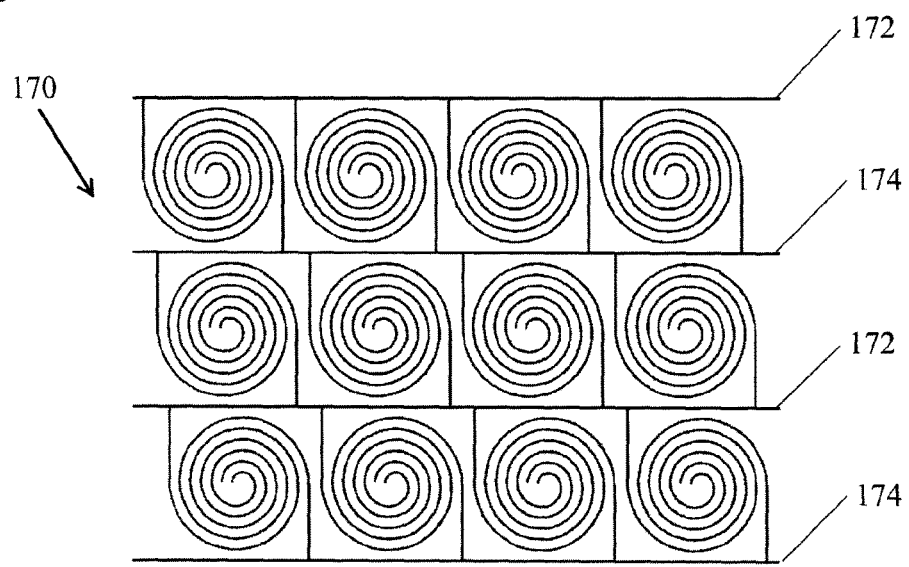
FIG. 7 is a schematic view of an interdigitated "jelly roll" pattern showing multiple levels of interdigitation, according to some embodiments of the present invention.

Referring to FIG. 6, a multilevel interdigitated SC electrode system ("jelly roll" configuration) is shown generally at 150. First electrode 152 and second electrode 154 describe a coiled configuration on a first substrate 156. A plurality of short 'digits' 166, 168 on each of the first and second electrodes interdigitate in the coiled configuration ("coiled", "coil together"). Leads (not shown) may connect first and second electrodes to an electrical system via contacts 158 and/or 160 (for the first electrode) and contacts 162 and/or 164 for the second electrode), to provide a voltage to the electrodes. FIG. 7 illustrates generally at 170 another embodiment of a multi-level interdigitated SC electrode system, comprising a plurality of 'jelly roll' subunits. First 172 and second 174 electrode pairs form an interlocking coiled pattern, providing a greater density of electrodes.

One of skill in the art would understand that other SC electrode system designs with multiple levels of interdigitation are also possible. Such multiple levels of interdigitation can be used to cover larger surface areas in cases where the surface area that needs to be covered is too large for a single interdigitated electrode pattern to cover. The bus bars themselves can also form an interdigitated electrode pattern as exemplified in FIG. 5. Additional levels of electrodes can also be created in the same or similar repeating patterns. In some embodiments, a thinner electrode structure can be used at the lower level of a hierarchical electrode system, and the bus bars can be wider for electrical conductivity. For example, in some embodiments, the smallest electrode structures can be 0.015 mm wide, while the bus bars are 0.05 mm wide.

One of skill in the art would understand that the specific interdigitated SC electrode system designs described above are only examples of suitable designs, and that other interdigitated patterns could also be used in the variable transmittance optical filters according to various embodiments. A worker skilled in the art would be able to determine specific interdigitated designs of the SC electrode system that are appropriate for certain applications. For example, interdigitated SC electrode systems similar to those exemplified in FIGS. 5 and 7 with multiple levels of interdigitation could be used in devices such as architectural smart windows and automotive smart windows, where the surface area of the window is larger. In contrast, interdigitated SC electrode systems exemplified in FIGS. 3, 6 and 9 could be used for round, oval, or other shaped devices such as ophthalmic lenses.

Figure 4:
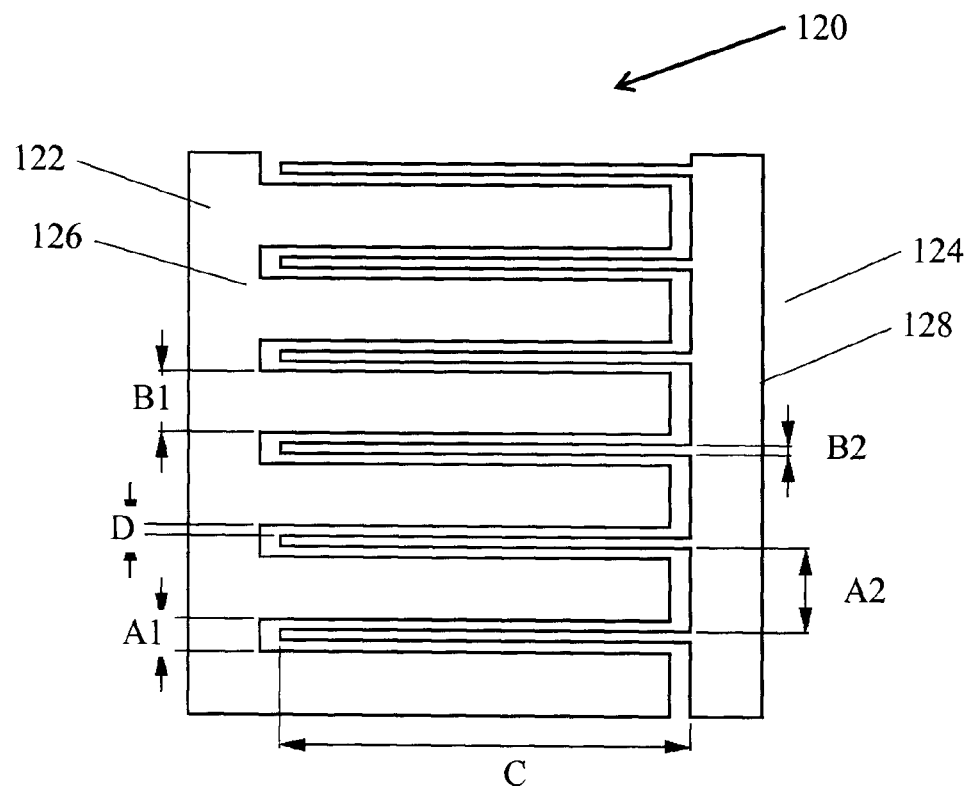
FIG. 4 is a schematic top view of an asymmetric interdigitated electrode structure according to some embodiments of the invention.

The finger-like structures of the first and second electrodes are separated by a predetermined separation distance (interdigit spacing D of FIGS. 1, 4). The predetermined separation distance may be an average distance, minimum distance, and/or maximum distance, and may be configured, along with other factors of the variable transmittance optical filter, in order to effect operation of the optical filter under predetermined conditions. For example, the separation distance may be configured so that application of a predetermined voltage to the electrodes effects a transition of the optical filter in a predetermined amount of time. The separation distance D between adjacent structures of the first and the second electrodes of the SC electrode system may vary depending on digit spacing (A) and/or digit width (B) or other factors. In some embodiments, D is less than 5 mm, or less than 1 mm, or less than 500 µm, or less than 50 µm, or less than 10 µm. In some embodiments, the predetermined separation distance between the anode and the cathode of the SC electrode system is from about 10 µm to about 5 mm, or from about 10 µm to about 100 µm, or from 10 µm to about 1 mm or from about 20 µm to about 70 µm, or from about 25 µm to about 50 µm, or any amount or range therebetween.

In embodiments of the present invention, the first and second electrodes are substantially electrically separate, although the distance between them may be small. For example, the transparent substrate upon which the electrodes are disposed may provide sufficient insulation even at the points of closest approach between anode and cathode. Likewise, gaps above the transparent substrate, in the plane of the electrodes, may be occupied by sufficiently insulating material, such as that of the transparent substrate, air, or the like. The distances between first and second electrodes, insulating material interposed therebetween, and operating voltage, may together be configured so as to limit current travelling through the insulating material to below a predetermined level, and/or to avoid dielectric breakdown of the insulating material. In an embodiment of the present invention, the sheet conductivity of the material (insulating material) between the electrodes is greater than about 100 Ohms, or greater than about 1000 Ohms, or greater than about 10 kOhms, or greater than about 1 MOhm, or from about 100 Ohms to about 1 MOhms or any amount or range therebetween.

In some embodiments, the SC electrode system of the variable transmittance optical filter comprises electrode structures with symmetric surface areas and/or widths, asymmetric surface areas and/or widths, or a combination thereof. FIGS. 1 and 4 illustrates dimensions digit spacing A, digit width B, digit length C, and separation distance D, for a system where the first and second electrodes are of substantially the same size and configuration, Dimensions A-D may be described as values (e.g. lengths or width) or as ratios of the dimension. For example, an SC electrode system where the first and second electrodes are of substantially equivalent width or area may be described as a width ratio of about 1:1, or as an area ratio of about 1:1.

According to some embodiments, digit spacing (A) and/or digit width (B) of each electrode may independently be any suitable dimension from about 0.001 mm to about 5 mm, or any amount or range therebetween, for example about 0.01 to about 0.05 mm, or 0.05 to about 0.1 mm, or about 0.1 mm to about 0.5 mm, or about 0.1 to about 1.0 mm. The first and second electrodes together may comprise from about 50% to about 99% of the substrate upon which they are disposed, or at least about 50%, 60%, 70%, 80%, 90% or 95% of the substrate upon which they are disposed. According to some embodiments, electrode features at different levels of a hierarchical electrode structure may have different widths.

In some embodiments, the SC electrode system is designed with substantially equal electrode widths, in which the width of the first electrode is approximately the same as the width of the second electrode (e.g. B1 is substantially equal to B2). In such embodiments, the predetermined separation distance is such that the electrodes structures are spaced closely together and the electrode width is small. The close spacing of the electrodes and the width of the electrodes can facilitate transitioning of the variable transmittance optical filter from one state of visible light transmittance to another if the electrodes are close enough to allow the change in the transition material over one electrode to "diffuse" over the nonconductive spaces between the electrodes.

FIG. 4 illustrates an embodiment where the first and second electrodes have different size and configuration (first and second electrodes are asymmetric). Referring to FIG. 4, another embodiment of a SC electrode system is shown generally at 120. This asymmetric electrode system comprises a first electrode 122 and second electrode 124, each comprising a plurality of digits. In the embodiment shown, the electrodes each comprise a bus bar portion 126, 128. Digit spacing (A1 and A2), digit width B1 and B2, digit length C and interdigit spacing D are indicated.

In the embodiment shown in FIG. 4, digit spacing of the first electrode (A1) is less than digit spacing A of the second electrode (A2); digit width of the first electrode (B1) is greater than digit width of the second electrode (B2). It will be appreciated that the description is also applicable to an embodiment where A1 is greater than A2 and/or B1 is less than B2 In this embodiment, digit length C and interdigit spacing D are substantially the same for both first and second electrodes. In an embodiment where one or both electrodes are of a curvilinear, or circumferential or other shaped layout, the relative areas of the first and second electrodes may be described. For embodiments where the electrodes are of differing width and/or spacing (asymmetric electrodes), a ratio of B1:B2 or vice versa may be from about 2:1 to about 10:1 or about 20:1 or about 30:1 or about 40:1, or about 50:1, or any amount or range therebetween, for example 2:1, 3.33:1, 5:1, 10:1, 20:1, or about 33:1. A ratio of A1:A2 or vice versa may be from about 2:1 to about 10:1 or about 20:1 or about 30:1 or about 40:1, or about 50:1, or any amount or range therebetween, for example 2:1, 3.33:1, 5:1, 10:1, 20:1, or about 33:1. In some embodiments, an asymmetric SC electrode pattern can provide improved uniformity of VLT over the area of the optical filter while transitioning from one state of visible light transmittance to another with fewer electrodes, or reduced surface area of electrodes. This may allow for simplification of manufacture (e.g. less rigorous etching or printing of narrow or fine electrodes. In some embodiments, one electrode of each pair of electrodes has a larger surface area and/or width than the other. Area of an electrode may be calculated by, for example, multiplication of the digit length C by digit width B. Thus, for a system with an asymmetric electrode configuration, B1×C1 is greater than B2×C2.

For an SC electrode system with asymmetric electrodes, the first and second electrodes may have a relative area of about 2:1 to about 1000:1, or any amount or range therebetween, for example about 3:1, about 5:1, about 10:1, about 20:1, about 40:1, about 80:1, about 90:1, about 100:1, about 200:1, about 300:1, about 400:1, about 500:1 about 750:1, or any amount or range therebetween. The first electrode may comprise from about 50 to about 99.9% of the area, or about 50, 55, 60, 65, 70, 75, 80, 85, 90, 95 or 99% of the area or any amount or range therebetween.

In some embodiments, the electrodes are configured and shaped so as to drive transitioning of the transition material over substantially the entire area of the optical filter. Interdigitation of electrodes may allow for a sufficient potential voltage difference to be applied in substantially all regions of the window to facilitate driving the transition substantially uniformly over the whole optical filter area.

In some embodiments, the SC electrode system is designed such that it comprises only two electrodes side by side (i.e. two finger-like structures of an interdigitated electrode). These electrodes may be the same width or different widths. If the widths of the electrodes each have a width, for example, within 25% of each other (e.g. width ratio of about, or less than, 1:1.25), and are in a first range, then an AC method of fading, as described elsewhere herein may be used in order to speed up transition from one state of visible light transmittance to another. The first range may be: greater than 1 m, greater than 100 mm, greater than 10 mm, greater than 1 mm, greater than 0.5 mm, greater than 0.1 mm, or greater than 0.05 mm. If the widths of the electrodes are different, the first electrode can be one or more orders of magnitude larger than the second electrode.

The first electrode may be an anode and the second electrode a cathode, or vice versa, depending on the polarity of the voltage applied. In one embodiment, for example, the SC electrode system may have most of its area at a positive potential (anode) and just a small area or a small strip at a negative potential that serves as the cathode. Such an embodiment may comprise two interdigitated electrodes, or "fingers" with one very wide anode finger and a thin cathode finger.

In some embodiments, the variable transmittance optical filter comprises an SC electrode system where the anode structures has a larger area than the cathode structures (the first electrode is an anode and the second electrode is a cathode). This type of electrode design may be used when the variable transmittance optical filter comprises a transition material in which a transition from one state of visible light transmittance occurs predominantly at or near the anode. In some embodiments, the variable transmittance optical filter comprises an SC electrode system where the cathode structures are wider than the anode structures (the first electrode is a cathode and the second electrode is an anode). This type of electrode design may be used when the variable transmittance optical filter comprises a transition material in which a transition from one state of visible light transmittance to another occurs predominantly at or near the cathode.

In some embodiments, where the cathode is wider than the anode, both the anode and the cathode are very narrow, and the difference in width between them is small.

In some embodiments, the voltage applied to a symmetric or asymmetric SC electrode system can be reversed in polarity one or more times in order to facilitate transition of the transition material from one state of visible light transmittance to another. Thus, the invention also provides for a method of transitioning a transition material from a first state of light transmission to a second state of light transmission comprising the steps of applying a positive voltage to a first electrode and a negative voltage to a second electrode and reversing the polarity of the voltage, thereby applying a negative voltage to the first electrode and a positive voltage to the second electrode. The first state of light transmission may be a dark state, and the second state of light transmission may be a faded, or light state.

The voltage can applied to the variable transmittance optical filter by connecting the source of electric voltage to the at least one pair of electrodes of the SC electrode system and the polarity of the voltage can be switched back and forth between the electrodes in each pair (essentially switching the anode and cathode back and forth between the two electrodes). This switching of polarity may allow for more rapid and even transition over the full area of the optical filter from one state of visible light transmittance to another. In some embodiments, where the variable transmittance optical filter comprises a transition material that is a hybrid P/E switching material, reversing the polarity of voltage applied to the electrodes of the SC electrode system results in completion of the transition from dark to light states.

Switching the polarity of the voltage can be done at fairly low frequency, for example, only once during the transition from one state of visible light transmittance to another or by applying an AC signal (AC power) to the variable transmittance optical filter, or by reversing a DC signal. In some embodiments, the switching frequency is the same order of magnitude as the reciprocal of the transition time of the optical filter. Alternatively, higher switching frequencies can be used. It will be readily understood that switching frequencies may be limited by capacitive effects induced by the electrode structure. This method allows wider and hence less expensive patterns of interdigitated electrodes to be used while still allowing full transition from one state of visible light transmittance to another over the interdigitated electrode area. Thus, in some embodiments, the variable transmittance optical filter comprises an SC electrode system in which the polarity of voltage is switched at a frequency of less than 2 kHz, or less than 1 kHz, or less than 0.5 kHz, or less than 0.1 kHz. In some embodiments, the variable transmittance optical filter comprises an SC electrode system in which the polarity of the voltage is switched at a frequency ranging from about 0.1 kHz to about 2 kHz, or any amount or range therebetween. In some embodiments, the variable transmittance optical filter comprises an SC electrode system in which the polarity of voltage is switched by the application of a square wave applied in a frequency of up to about 1 kHz.

In some embodiments, the polarity can be switched periodically or quasiperiodically to produce an applied voltage generally characterized by a square wave with a predetermined maximum voltage, minimum voltage, duty cycle, and average. In one embodiment, maximum and minimum voltage levels obtained by the square wave include −2 V and +2 V and/or 1 V and 3 V, and/or 0.5 V and 5 V, and/or 0.1 V and 10 V, and/or 0.001 V and 140 V; or any amount or range therebetween. It would be readily understood that other voltage levels may be suitable.

1.2.3 Preparation of SC Electrode System

The SC electrode system can be prepared according to methods known in the art. Typically, the transparent conductive material is disposed on the substantially transparent substrate of the first layer of the variable transmittance optical filter. The desired pattern of electrodes may be etched into the electrically conductive material by processes known in the art, such as additive photolithography, subtractive photolithography, silk screening, milling, engraving, vapour deposition, electroplating and wet (for example, HCl) or dry (for example, $CH_4$, $O_2$, HBr, $Cl_2$, and the like) etching techniques. As is known in the art, pulsed laser techniques can also be used to pattern the electrically conductive material. Additive processes such as drop on demand printing or masking and then depositing material in the non-masked areas to form the electrodes are also suitable for preparing the SC electrode system according to the present invention. In embodiments where the SC electrode system is designed with asymmetric electrode widths, the number of very thin electrodes that need to be etched may be reduced. As such, in some embodiments, variable transmittance optical filters having an SC electrode system with asymmetric electrode widths may be less expensive to manufacture.

The etching processes described above use a substrate with a conductive coating as the starting point. Methods of applying the electrically conductive material to the substrate to form suitable conductive layers are well known in the art. For example, substrate materials pre-coated with indium tin oxide (ITO) are available from a number of suppliers, including CP Films of St. Louis, Mo. and Southwall Technologies Inc. of Palo Alto, Calif. (now Solutia Inc. St. Louis Mich.). One skilled in the art will recognize that multiple layers of conductive materials can also be employed in the optical filter of the present invention.

The conductive layers are disposed on the substrate as a coating. The conductive layer is coated or deposited onto the substrate to a thickness that provides adequate conductance for the optical filter, and which does not appreciably interfere with the required transmission of light. In one embodiment, the thickness of the conductive layer ranges from about 1 nanometer to about 90 microns. In another embodiment, the thickness of the conductive layer ranges from about 10 nanometers to about 10 microns.

2. Second Layer Comprising a Transition Material

As indicated above, the variable transmittance optical filter with an SC electrode system comprises a second layer proximate to the first layer, the second layer comprising a transition material capable of dynamically varying the degree of visible light transmittance. The transition material can be a material or system known in the art. Exemplary, non-limiting transition materials include those used in electrochromic, liquid crystal, and suspended particle technologies. In some embodiments, the transition material can be a hybrid photochromic/electrochromic switching material, and may comprise a hybrid photochromic/electrochromic compoundas exemplified herein.

The state of visible light transmittance can include a dark state, a light state, an opaque state, or a clear state. For example, many electrochromic technologies result in a change from a dark state to a light state, or vice-versa. Liquid crystal technologies typically result in a change between a clear state and a translucent or opaque state. Suspended particle technologies result in a change from a light state to a dark state.

In embodiments where there is no optional third layer, and thus only one substantially transparent substrate, the transition material is disposed on the surface of the substantially transparent substrate, and in contact with the SC electrode system. In other embodiments where the variable transmittance optical filter comprises a third layer that is a substantially transparent substrate, the transition material is disposed between the first layer and the third layer and in contact with the SC electrode system.

2.1 Hybrid Photochromic/Electrochromic Switching Material

In one embodiment, the variable transmittance optical filter of the invention comprises a transition material that is a hybrid photochromic/electrochromic ("hybrid P/E")

switching material. A hybrid P/E switching material has both electrochromic and photochromic properties. A hybrid P/E switching material may darken (e.g. reach a 'dark state') when exposed to light from a light source, and may lighten ("fade", "electrofade", "bleach", "electrobleach", achieve a "light state") when exposed to an electric charge. Such a switching material may be alternately described as an auto-darkening material. In some embodiments, the switching material may fade upon exposure to selected wavelengths of visible (VIS) light, without sacrifice of the ability to be electrofaded when restored to a darkened state.

In some embodiments, the hybrid P/E switching material is a liquid, a solid, a sol-gel or a gel. The liquid, sol-gel or gel may be of a range of viscosity.

The thickness of the layer of hybrid P/E switching material may affect the transmittance of the variable transmittance optical filter of the invention and may be selected depending on the particular application desired. For example, when comparing a thinner and a thicker layer of hybrid P/E switching material comprising the same concentration of dye, the thicker layer will provide a lower percentage visible light transmission in the dark state. In some embodiments of the invention, the hybrid P/E switching material has a thickness from about 0.1 microns to about 10,000 microns; or from about 1 to about 1000 microns; or from about 10 microns to 100 microns, or any amount or range therebetween. Typically, uniform thickness of the hybrid P/E switching material will be desired in most applications; however, it is contemplated that a variable transmittance optical filter of the invention can comprise a non-uniform thickness of the hybrid P/E switching material for applications where some darker regions and some lighter regions are desired.

The hybrid P/E switching material comprises a hybrid P/E compound ("hybrid dye", "hybrid chromophore")) that has a dark state and a light state. In certain embodiments, the hybrid P/E switching material, may comprise one or more optional components. For example, the hybrid P/E switching material may further comprise one or more of a solvent, an electrolyte, a polymer, a charge compensator, a charge carrier, a UV stabilizing agent, a UV blocking agent, a tinting agent, or the like. One skilled in the art will recognize that certain components may be able to fill dual roles in the hybrid P/E switching material, for example, certain dyes may self-polymerize and fulfill the role of both dye and polymer; certain polymers may also have UV blocking capabilities; or the like. Conversely, in some embodiments, a given component may be made up of several individual compounds, e.g., the polymer component may be a copolymer comprising different monomeric units.

In one embodiment, the hybrid P/E switching material of the invention comprises a chromophore and a component in which the chromophore is soluble such as a solvent or a polymer, or a polymer that fulfills the function of a solvent. In another embodiment, the hybrid P/E switching material of the invention comprises a chromophore, a solvent, and at least one optional component selected from the group consisting of: a) an electrolyte; b) a polymer component; c) a charge compensator; d) a charge carrier; e) a UV stabilizing agent; f) a UV blocking agent; and g) a tinting agent.

Hybrid P/E Compounds:

The hybrid P/E switching material according to the present invention comprises one or more organic compounds ("dyes" or "chromophores") that exhibit both photochromic and electrochromic characteristics. These dual mode compounds are capable of reversibly switching between two distinct isoforms when stimulated electrically and by light.

The hybrid photochromic/electrochromic compounds that can be used in the present invention are organic, and include classes of compounds from the hexatriene family, for example, the class of compounds known in the art as diarylethenes, dithienylcyclopentenes, and fulgides. In some embodiments, switching of the compound to the ring-open form is induced by application of a voltage to a switching material comprising the compound, and is independent of the polarity of the applied voltage. The hybrid P/E compound may be an anodic species, that is, the electrochromic colour change (electrochromic fading, electrochromic transition from a dark state to a light state) occurs primarily at the anode. The hybrid P/E compound may from a faded state to a dark state when exposed to light of a wavelength comprising a portion of the UV range, for example from about 300 to about 450 nm, or any amount or range therebetween, for example from about 350 to about 420 nm, or from about 365 to about 420 nm, or from about 375 to about 420 nm, or from about 375 to about 420 nm, or from about 380 to about 420 nm, or from about 385 nm to about 420 nm, or any amount or range therebetween.

According to one embodiment of the invention, the hybrid P/E switching material comprises one or more chromophores from the class of compounds known as diarylethenes. Examples of diarylethenes include derivatives of 1,2-dithienylcyclopentene as described in International Patent Publication No. WO 2004/1015024, having the general structure of Formula 1 below:

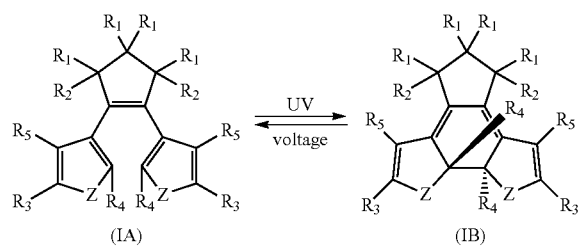

(IA)    (IB)

wherein each $R_1$ is independently H or a halogen;

Z is N, O or S;

wherein each $R_2$ is independently H, a halogen, or both $R_2$ when taken together form CH=CH, or when in polymeric form $R_2$ is CH—CH and forms part of a polymer backbone;

wherein each $R_3$ is independently alkyl, aryl, H, a halogen or $CO_2Y$ (Y=H, Na, alkyl, aryl);

wherein $R_4$ is aryl; and wherein each $R_5$ is independently H, alkyl or aryl.

"Aryl" includes substituted or unsubstituted benzyl or thiophenyl. Substitutions may be alkyl, halogen or the like. Benzyl may be substituted in ortho-, meta- or para-positions of the benzyl ring. Thiophenyl may be substituted at one or more of positions 2, 3, 4 or 5 of the thiophene ring.

"Halogen" includes F, Br and Cl.

"Alkyl" includes methyl, ethyl, propyl, butyl, t-butyl.

Preparation of exemplary fluorinated dithienylcyclopentene derivatives that may be incorporated in the switching materials of the invention follows the general methodology of Scheme 1 below:

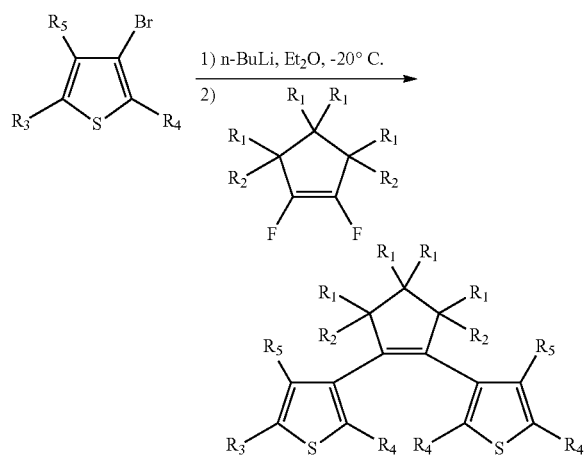

In one embodiment of the invention, the switching material comprises compounds of Formula 1 wherein $R_1$ and $R_2$ are F, $R_3$ and $R_4$ are

(X=S), and $R_5$ is H. In another embodiment of the invention, the switching material comprises compounds of Formula 1 wherein $R_1$ and $R_2$ are F, $R_3$ is H, $R_4$ is

(X=S), and $R_5$ is H.

In a further embodiment of the invention, the switching material comprises compounds of Formula 1 wherein $R_1$ and $R_2$ are F, $R_3$ and $R_4$ are independently

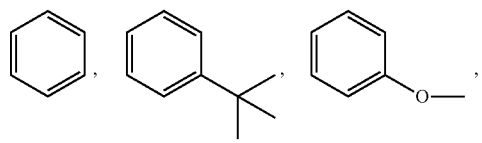

or and, and $R_5$ is H. In another embodiment of the invention, the switching material comprises compounds of Formula 1 wherein $R_1$ and $R_2$ are F, $R_3$ is H, $R_4$ is

and $R_5$ is H. In a further embodiment of the invention, the switching material comprises compounds of Formula 1 wherein $R_1$ and $R_2$ are F, $R_3$ is

(X=S), $R_4$ is $CH_3$, and $R_5$ is H. In another embodiment of the invention, the switching material comprises compounds of Formula 1 wherein $R_1$ and $R_2$ are F, $R_3$ is

(X=S); $R_4$ is $CH_3$, and $R_5$ is H.

The chromophores can be incorporated into the switching material in monomeric or polymeric forms depending on the functional demands required. The compounds of Formula 1 may be incorporated in polymeric form as part of the polymer backbone or as a pendant group. For example, fluorinated compounds may be polymerized using ring-opening metathesis polymerization in accordance with Scheme 2 below:

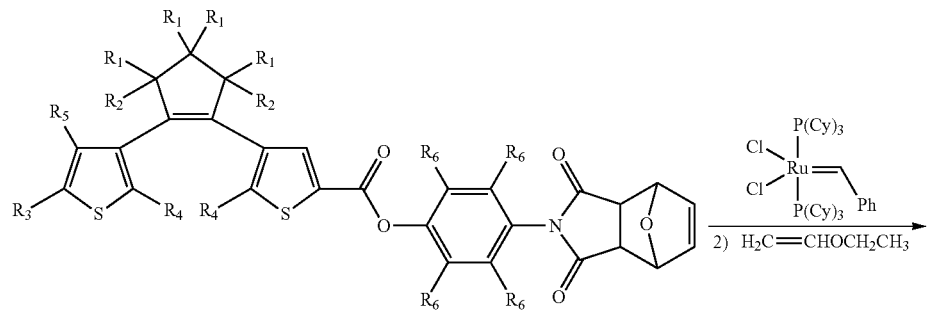

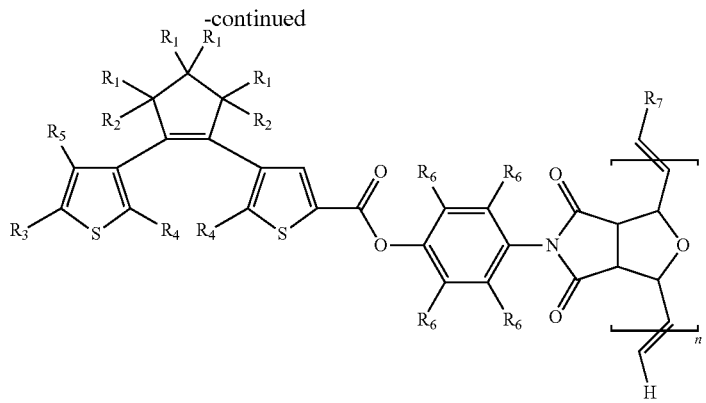

Exemplary non-fluorinated dithienylalkene derivatives that may be incorporated in the switching materials of the invention can be prepared in accordance with the general methodology of Scheme 3 below:

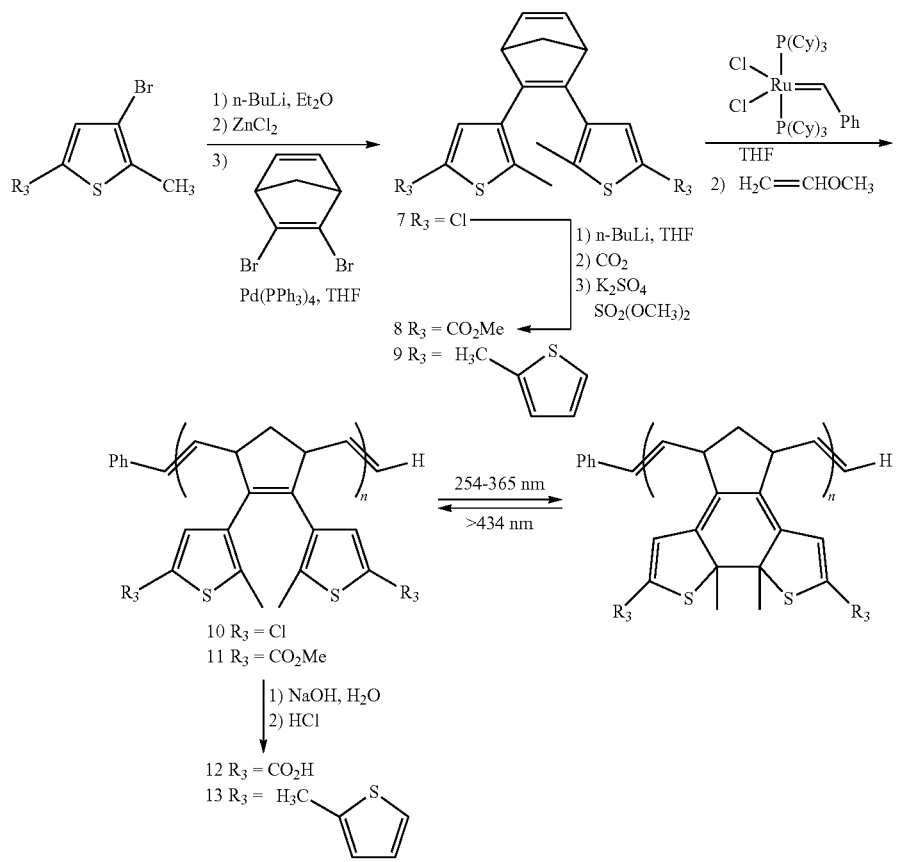

In one embodiment of the invention, the switching material comprises a compound of Formula 1 wherein $R_1$ is H, $R_2$ is CH=CH, $R_3$ is Cl, $R_4$ is $CH_3$, and $R_5$ is H. In another embodiment of the invention, the switching material comprises a compound of Formula 1 wherein $R_1$ is H, $R_2$ is CH=CH, $R_3$ is $CO_2CH_3$, $R_4$ is $CH_3$, and $R_5$ is H. In a further embodiment of the invention, the switching material comprises a compound of Formula 1 wherein $R_1$ is H, $R_2$ is CH=CH, $R_3$ is (X=S), $R_4$ is $CH_3$, and $R_5$ is H.

In other embodiments of the invention, the switching material comprises a compound of Formula 1 wherein the compound forms part of a polymer. In one embodiment of the invention, $R_1$ is H, $R_2$ is CH=CH and forms part of the polymer backbone, $R_3$ is Cl, $R_4$ is $CH_3$, and $R_5$ is H. In a further embodiment of the invention, the switching material comprises a compound of Formula 1 wherein $R_1$ is H, $R_2$ is CH=CH and forms part of the polymer backbone, $R_3$ is $CO_2CH_3$, $R_4$ is $CH_3$, and $R_5$ is H. In another embodiment of the invention, the switching material comprises a compound of Formula 1 wherein $R_1$ is H, $R_2$ is CH=CH and forms part of the polymer backbone, $R_3$ is $CO_2H$, $R_4$ is $CH_3$, and $R_5$ is H. In another embodiment of the invention, the switching material comprises a compound of Formula 1 wherein $R_1$ is H, $R_2$ is CH=CH and forms part of the polymer backbone, $R_3$ is

(X=S), $R_4$ is $CH_3$, and $R_5$ is H.

An example of a suitable chromophore for inclusion in the hybrid P/E switching material is one that exhibits both photostability as well as electrochemical durability. The photostability of a compound, e.g., the resistance of the chromophore to light induced degradation, can be measured by the amount of time it takes for the compound to degrade to a certain point under constant light exposure. For example, in one embodiment the compound can be measured in its dark state and its light state to determine its contrast ratio prior to testing. During testing, the contrast ratio is monitored periodically to determine degradation. Failure can be determined to occur when the contrast ratio falls below a certain level, or when the contrast ratio falls below 50% of the original contrast ratio. Other methods for testing are within the knowledge of persons skilled in the art. The photostability of embodiments of the invention can be tested using a Xenon-arc lamp, for example in a Q-Sun testing unit made by Q-Lab of Cleveland, Ohio. In one embodiment, the hybrid P/E switching material of the invention comprises a chromophore having a photostability in the range of about 1000 hours to about 5000 hours, or over 5,000 hours of constant light exposure. The electrochemical durability of a suitable chromophore is measured as the number of cycles that the chromophore can maintain its switching activity between the light and dark state. In one embodiment, the hybrid P/E switching material of the invention comprises a chromophore having an electrochemical durability in the range of about 1000 to about 5,000 cycles or over 5,000 cycles. Typically, the hybrid P/E switching material according to the present invention contains (by weight) 0.05% to about 30%, or any amount or range therebetween, for example about 1, 2, 3, 4, 5, 6, 7, 8, 9, 10, 11, 12, 13, 14, 15, 16, 17, 18, 19, 20, 21, 22, 23, 24, 25, 26, 27, 28 or 29%.

Examples of selected hybrid P/E compounds include: S001, S002, S042, S054 and S068; or derivatives thereof having different functional groups of the peripheral benzyl or thiophene rings.

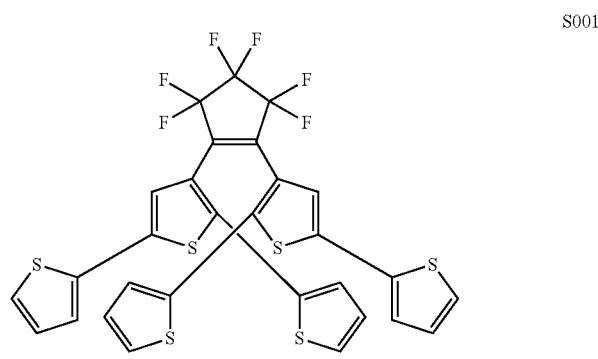

S001

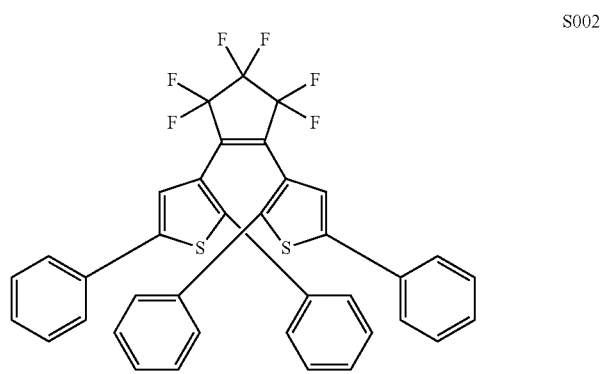

S002

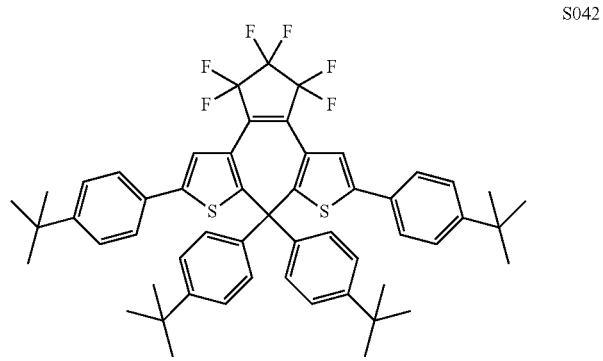

S042

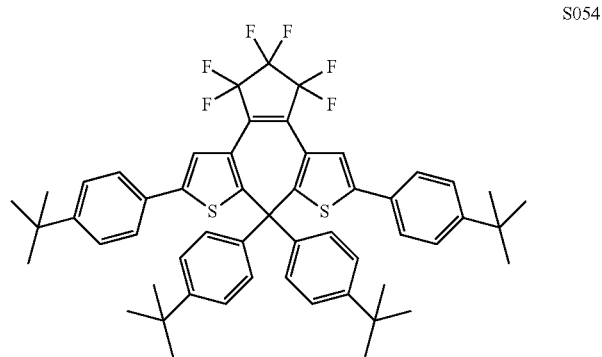

S054

S068

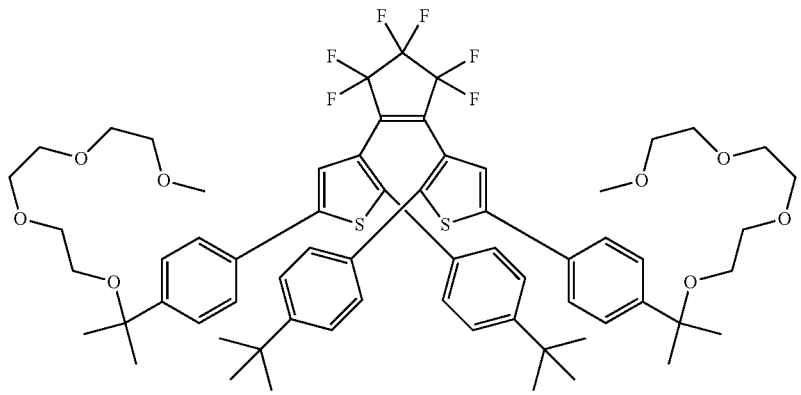

Solvent:

The solvent component of the hybrid P/E switching material dissolves, intersperses and/or diffuses the one or more chromophores and other components throughout the hybrid P/E switching material. The solvent used in the preparation of the switching material is typically inert, i.e., photochemically and electrochemically inactive, and colourless, and has a sufficiently high boiling point to prevent solvent loss under typical operating conditions. Examples of suitable solvents include, but are not limited to, triglyme, dichloroethane, tetraglyme, propylene carbonate, ethylene carbonate, water, butyrolactone, cyclopentanone and mixtures thereof. In one embodiment of the present invention, the solvent component comprises triglyme.

One or more solvents may be present in a switching material in an amount from about 50% to about 95% (by weight), or any amount or range therebetween, for example 50, 60, 70, 80 or 90%, or any amount or range therebetween.

Electrolyte:

Electrolytes are generally electrically conductive, and may include alkali metal salts, tetralkylammonium salts or the like. Examples of electrolytes include $TBABF_4$ (tetrabutylammonium tetrafluoroborate), $TBAPF_6$ (tetrabutylammonium hexafluorophosphate), tetrabutylammonium perchlorate, lithium bis(trifluoromethane sulfonimide), lithium triflate, LiBOB (lithium bis(oxatlato)borate), $LiClO_4$ (lithium perchlorate) or the like. The one or more electrolytes may be present in an amount from about 0.1% to about 10% (by weight) or any amount or range therebetween, for example 1, 2, 3, 4, 5, 6, 7, 8, or 9%. Where the solvent is an ionic solvent, an electrolyte component may be optional.

Polymer Component:

In some embodiments of the invention, one or more polymers or sol-gels may be included in the compositions. Examples of polymers include polyvinylbutyral (PVB) B-90, PVB-B72, poly(methyl methacrylate) (PMMA), nitrile rubber (NBR), polyvinylpyrrolidone (PVP), polyvinylidene fluoride (PVDF), poly(dimethylsiloxane) (PDMS), poly(ethyl methacrylate) (PEMA), The one or more polymers or sol-gels may be present in an amount from about 0.1% to about 30% (by weight) or any amount or range therebetween, for example 1, 2, 3, 4, 5, 6, 7, 8, 9, 10, 12, 14, 16, 18, 20, 22, 24, 26, 28 or 30%, or any amount or range therebetween. In some embodiments the one or more polymers or sol-gels may function as a rheology modifier.

Charge Compensator:

In some embodiments of the invention, a charge compensator (charge-transfer complex or charge-transfer salt) may be included in one or more compositions. A charge compensator may be a cathodic material to aid in redox balance of an anodic chromophore. The charge compensator may be stable, or sufficiently stable in both reduced and oxidized forms. The charge compensator may be an organic semiconductor. Examples of charge compensators include Prussian Blue (PB), ferrocenium tetrafluoroborate, ferrocenium hexafluorophosphate, tetracyanoquinodimethane, tetrafluoro-tetracyanoquinodimethane, 1,4-dicyanobenzene, 1,2,4,5-tetracyanobenaene, pyrene, tetracene, pentacene or the like. The one or more charge compensators may be present in an amount from about 0.1% to about 10% (by weight) or any amount or range therebetween, for example 1, 2, 3, 4, 5, 6, 7, 8, or 9%

Charge Carrier:

The primary role of the charge carrier component is to facilitate transport of the electrons and "holes" between the two electrodes and consists of, or any combination of, substances known in the art to be suitable charge carrier materials. The charge carrier used in the preparation of the hybrid P/E switching material is typically redox active in the electrochemical potential range required to trigger colour lightening of the hybrid P/E switching material. Examples of suitable charge carriers include, but are not limited to tris(4-bromophenyl) amine, tris(4-chlorophenyl) amine, 10-methylphenothiazine, 9,9-(N,N,N',N'-tetrabiphenyl-N,N'-diphenyl)fluorene, 4,4'-di(N-carbozolyl)biphenyl, 1-(N-carbozolyl)-4-diphenylaminobenzene, N,N,N'N'-tetraphenylbenzidine, and 1-(N-Carbozolyl-4-N'-alpha-naphthyl-N'-phenylamine. The hybrid P/E switching material according to the present invention typically contains about 0.1% to about 10% by weight of the charge carrier component UV Stabilizer:

The primary role of the UV stabilizer is to inhibit photodegradation of the hybrid P/E switching material by scavenging radical intermediates formed in photodecomposition processes and consists of, or any combination of, substances known in the art to be suitable UV stabilizing materials. Examples of suitable UV stabilizers include, but are not limited to the class of compounds known in the art as hindered amine light stabilizers (HALS). One or more UV stabilizers may be present in an amount from about 0.01% to about 10% (by weight) or any amount or range therebetween, for example 1, 2, 3, 4, 5, 6, 7, 8, 9 or 10%.

UV Blocker:

The primary role of the UV blocker (or UV absorber) is to prevent photodegradation of the auto-darkening material by including a component of the material that absorbs higher energy UV light and dissipates the energy thermally preventing photodecomposition and consists of, or any combination of, substances known in the art to be suitable UV blocking materials. Examples of suitable UV blockers include, but are not limited to benzotriazoles, benzophenones. One or more UV absorbers may be present in an amount from about 0.01% to about 10% (by weight) or any amount or range therebetween, for example 1, 2, 3, 4, 5, 6, 7, 8, or 9%.

Tinting Agent:

Inclusion of a colourant or tinting agent in a composition according to various embodiments of the invention may achieve a desired colour and/or adjust the visible light transmission of the composition. A variety of colourants are known in the art, and selection of a colourant to achieve a desired colour, hue or transmissibility is within the ability of a skilled worker. Examples of colourants include one or more chromophores as described herein, Prussian blue, or the like. One or more colourants may be present in an amount from about 0.01% to about 10% (by weight) or any amount or range therebetween, for example 1, 2, 3, 4, 5, 6, 7, 8, or 9%

Although the optional components noted above have been described with reference to the hybrid P/E switching material as transition material, one of skill in the art would understand that some of these optional components could also be used when the variable transmittance optical filter comprises a transition material other than a hybrid P/E switching material.

2.2 Electrochromic Transition Materials

In one embodiment, the variable transmittance optical filter comprises an electrochromic transition material. Several technologies are well known in the art with respect to the design of electrochromic transition materials. Electrochromic transition materials generally comprise three central components: an ion storage component, ion conducting component and electrochromic component. Electrochromic transition materials typically function as the result of transport of charged ions from the ion storage component, through the ion conducting component into the electrochromic component by applying a voltage. The presence of the ions in the electrochromic component changes its optical properties, causing it to absorb visible light, the result of which is to darken the window. To reverse the process, the voltage is reversed, driving the ions in the opposite direction, out of the electrochromic component, through the ion conducting component, and back into the ion storage component. As the ions migrate out of the electrochromic component, it brightens (or "bleaches"), and the window becomes transparent again.

Several electrochromic components are known in the art and commercially available and include the organic electrochromic components PEDOT (poly(3,4-ethylenedioxythiophene)), PEDOT:PSS (poly(3,4-ethylenedioxythiophene) poly(styrenesulfonate)), polyaniline, polypyrrole, viologen or mixtures thereof. Nonlimiting examples of suitable inorganic electrochromic components include $WO_3$, NiO and $IrO_2$. These electrochromic components are suitable for inclusion in the electrochromic transition material of the variable transmittance optical filter. Thus in some embodiments the variable transmittance optical filter comprises a transition material having an inorganic electrochromic component. In other embodiments, the variable transmittance optical filter comprises a transition material having an organic electrochromic component.

The ion storage component of the electrochromic transition material can be one of many known in the art. Several non-limiting examples of suitable ion storage components include: nickel oxide (NiO), vanadium oxide ($V_2O_5$) or iridium oxide ($IrO_2$).

The ion conducting component of the electrochromic transition material can be one of many known in the art. The ion conducting component comprises an electrolyte, and can be a solid state or a liquid/polymer gel type component depending on the type of electrolyte used. For liquid type layers, an electrolyte is typically dissolved in a liquid solvent, for example, water or organic solvents (e.g. propylene carbonate, dimethylsulfite, nitromethane, etc.). For polymer gel type layers, an electrolyte is typically dispersed in a gel-forming polymeric matrix.

Suitable electrolytes that may be used include, for example, lithium-containing electrolytes or proton-based electrolytes. With proton-based electrolytes the coloring/bleaching processes of the electrochromic device are much faster since the ionic diffusivity of protons is about two orders of magnitude higher than that of lithium ions, thereby making. Lithium-containing electrolytes include, for example, $LiClO_4$/propylene carbonate liquid electrolyte, a polymer gel-type electrolyte comprising $LiClO_4$ with gamma-butyrolactone (GBL) and crosslinked methacrylated polyethylene oxide, oxymethylenelinked polyethylene glycol or amorphous polyethylene oxide with lithium trifluoromethylsulfonyl imide (LiTFSI), $LiAlF_4$, $LiNbO_3$, and the like. Proton-based electrolytes include, for example, Nafion™ ($C_7HF_{13}O_5S.C_2F_4$, polyacrylamido-methyl-propane sulfonic acid (poly-AMPS), polystyrene sulfonic acid (poly-SSA), polyethylene sulfonic acid (poly-ESA), $Ta_2O_5.pH_2O$, $SiO_2.pH_2O$, phosphotungstic acid (PWA), zirconium phosphate (ZP) and $Sn(NaH)(PO_4)_2.pH_2O$.

Additional protective components may be utilized in the electrochromic transition material to improve durability of the variable transmittance optical filter. For example, inorganic films, such as $Ta_2O_5$, $Sb_2O_5$, or nonporous polymer films, such as ultraviolet light-cured plasticized poly (vinyl alcohol), may be used to coat the electrochromic component to further protect the electrochromic layer from degradation due to contact with the ion conducting layer.

Methods of depositing electrochromic transition material on the substantially transparent substrate are known in the art, for example, sputtering, chemical vapour deposition or the like.

2.3 Other Transition Materials

Other transition materials such as, for example, liquid crystal materials and suspended particle materials are known in the art, and may be suitable for use in the variable transmittance optical filters according to the present invention. One of skill in the art would be able to select additional suitable transition materials capable of transitioning from one state of visible light transmittance to another that would be suitable for use with the SC electrode system of the variable transmittance optical filters of the invention.

The thickness of the optical filter according to various embodiments of the present invention may vary depending on the thickness and nature of the transition material, substrate, conductive layer and any other optional layers or components (optional 3rd layer, films or the like). Thinner optical filters may provide greater flexibility and/or faster fade times, while thicker optical filters may offer darker colour and/or greater rigidity. In accordance with one embodiment, the thickness of the optical filter is from about 10 to about 1000 microns, or from about 25 microns to about 250 microns, or from about 25 to about 125 microns, or any amount or range therebetween.

3. Control Circuit

To be operated, the variable transmittance optical filter of the present invention is connected to a power source capable of establishing a potential difference (voltage) between the electrodes of the SC electrode system of the variable transmittance optical filter. In some embodiments, the SC electrode system further comprises one or more bus bars to carry current from a power source to the electrodes. A control circuit can be used to switch the electrical voltage on or off based on input from an automated or semi-automated device (e.g. an irradiance meter, thermometer), a building environmental control system, a user or some other input, and can also be used to modulate the voltage to a predetermined level. The power for turning the variable transmittance optical filter on or off can come from a variety of sources, including an AC line voltage in a house or other building, a DC power source (e.g. a battery), an energy harvesting power source or the like. Examples of energy harvesting power sources include photovoltaic devices (e.g. solar cells, solar panels, or arrays thereof, photoelectric cells or arrays and the like); vibrational-energy harvesting technologies such as piezoelectrics; mechanical energy converters such as acoustic converters; thermal energy-harvesting devices such as pyroelectric or thermoelectric devices; or the like. The power source is connected to the variable transmittance optical filter through the control circuit. The control circuit may comprise a switch, such as a transistor, relay, or electromechanical switch that opens and closes the circuit between the power source and the interdigitated electrodes in the variable transmittance optical filter. The control circuit can also include an AC-DC and/or DC-DC converter for converting the voltage from the power source to an appropriate voltage to cause a change in the visible light transmittance of the variable transmittance optical filter. The control circuit may comprise a DC-DC regulator for regulation of the voltage. The control circuit can also comprise a timer and/or other circuitry elements for applying electric voltage to the variable transmittance optical filter for a fixed period of time following the receipt of input.

Depending on the transition material used in the variable transmittance optical filter, the application of voltage to the transition material will cause the transition material to either lighten or darken (e.g. if the transition material is an electrochromic transition material), or to lighten if the transition material is a hybrid P/E switching material.

Figure 8:
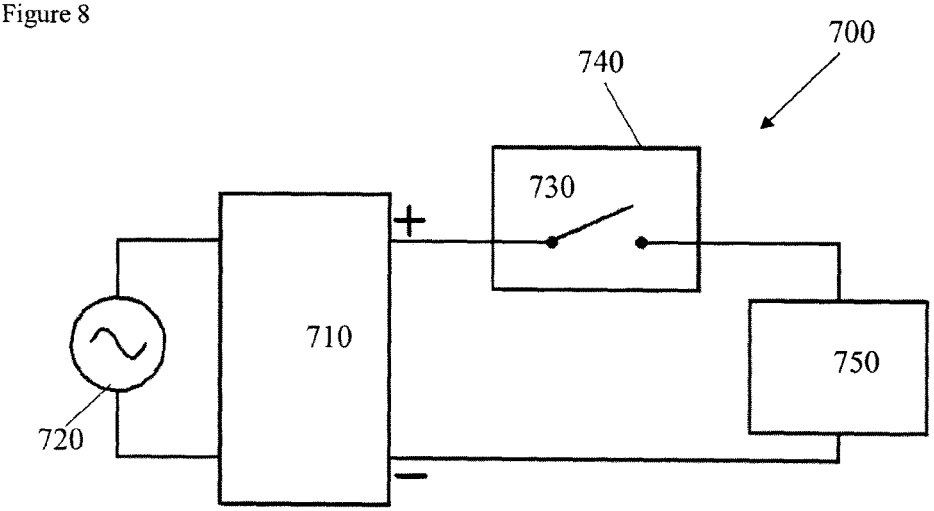
FIG. 8 illustrates an exemplary control circuit configuration for use with a variable transmittance optical filter according to some embodiments of the present invention.

Referring to FIG. 8, a control circuit shown generally at 700 may be used to apply a voltage to the interdigitated electrodes of the variable transmittance optical filter. A power source 720 supplies electric power to the circuit. In one embodiment, the power source 720 is an AC line voltage typically found in a home or commercial building. Optional AC transformer 710 can be used to transform the AC voltage into a DC voltage for use in the control circuit. Control electronics 740 comprising a switch 730 can be used to connect and disconnect the DC voltage from the variable transmittance optical filter 750. In embodiments where the power source provides DC current, an AC transformer may not be required. A power source may be a a building or vehicle electrical system, a battery, or an energy harvesting device, such as a photovoltaic power source.

Embodiments of the invention include switches that can be activated manually or automatically in response to predetermined conditions. For example, control electronics may process information such as time of day, ambient light levels detected using a light sensor, user input, stored user preferences, occupancy levels detected using a motion sensor, or the like, or a combination thereof, the control electronics configured to activate switches for applying voltage to the electrodes in response to the processed information in accordance with predetermined rules or conditions. In one embodiment, the power control electronics comprises a user-activated switch that passes the DC voltage from the power source substantially directly to the variable transmittance optical filter. The user activated switch can be a normally-open push button, or another type of switch. A switch may be configured to remain closed for a predetermined amount of time following actuation, thereby facilitating application of voltage to the optical filter for sufficient time to effect a state transition.

In some embodiments, a generated DC voltage, for example via an AC-DC transformer or converter, and/or a DC-DC converter or regulator, is matched to the voltage required by the variable transmittance optical filter in order to trigger a transition from one state of visible light transmittance to another. The voltage that can be applied in order for the variable transmittance optical filter to transition from one state of visible light transmittance to another will depend on factors such as the transition material and the resistivity of the electrodes of the SC electrode system. The voltage may be fixed or it may be controllable by the control system. In some embodiments where the transition material is a hybrid P/E switching material, the voltage applied ranges from between about 1 to about 12 volts DC. In another embodiments where the transition material is a hybrid P/E switching material, the voltage applied ranges from about 0.1 to about 42 volts DC. In other embodiments where the transition material is a hybrid P/E switching material, the optical filter of the invention lightens with the application of less than about 12 V, or less than about 6V or less than about 3 V, or less than about 2 V, or any amount or range therebetween, In some embodiments the amount of voltage applied to electrofade the switching material is from about 0.5 to about 3 V, or from about 1.2 to about 2.5 V or from about 1.8 to 2.1 V. In some embodiments of the invention, a minimum voltage is approximately 1.8 volts.

In some embodiments wherein the transition material is an electrochromic material, the variable transmittance optical filter will transition from one state of visible light transmittance to another with the application of a DC voltage in the range of about 3 V to about 5 V. In some embodiments where the transition material is a liquid crystal or suspended particle material, the variable transmittance optical filter will transition from one state of visible light transmittance to another, at higher DC or AC voltages, such as for example, 120 V AC.

In one embodiment of the invention, power control electronics 740 can be used to control the voltage being applied to the variable transmittance optical filter 750 of the present invention as well as for controlling the duration that the voltage is applied. In one embodiment, control electronics may include a DC-DC converter for converting and/or regulating the voltage from AC transformer 710. For example, AC transformer 710 may output a 12 Volt DC voltage. A DC-DC converter can be used to step the 12 Volt DC voltage down to a lower voltage. In one embodiment, the variable transmittance optical filter of the present invention uses a voltage in the range of 1.2 Volts to 2.1 Volts to transition from one state of visible light transmittance to another.

In another embodiment, the power control electronics 740 controls switch 730. In this embodiment, the power control electronics 740 close switch 730 in response to user input or input from an electronic device such as a sensor. The user presses a button connected to a normally open momentary switch to provide an input signal to power control electronics 740. The power control electronics 740 then closes switch 730 for a fixed period of time. The fixed period of time can be preset and built into the power control electronics by using a standard timing circuit familiar to those skilled in the art of electronic circuits. The fixed period of time would be preset to be the amount of time required for the variable transmittance optical filter 750 to transition from one state of visible light transmittance to another.

In some embodiments, a light sensor can also be incorporated into power control electronics 740 to sense when it is bright outside. For example, in embodiments including a light sensor, where a hybrid P/E transition material is used in the variable transmittance optical filter, if it is bright outside and the user presses the button, the power control electronics can maintain a voltage on the variable transmittance optical filter 750 in order to maintain the lightened state. Maintaining a voltage on variable transmittance optical filter 750 can serve to over-ride the auto-darkening aspect of the variable transmittance optical filter (e.g. when exposed to some wavelengths of light) and keep it in a light state even when it is exposed to UV light. In such embodiments, the user returns the variable transmittance optical filter to its normal auto-darkening state by pressing the button again, or by pressing a second button.

In some embodiments, for example where the transition material of the variable transmittance is a hybrid P/E switching material, the power control electronics may be configured to switch the polarity of the voltage applied to the variable transmittance optical filter one or more times, or to otherwise vary the applied voltage. In some embodiments, the voltage polarity may be switched between a positive and a negative polarity using a double pole double throw switch, or a collection of transistors, relays, or other electrical or electromechanical switches configured to switchably provide a first circuit path and a second circuit path. The first circuit path connects the electrodes to the DC power source such that a voltage measured from first electrode to second electrode is positive, while the second circuit path connects the electrodes to the DC power source such that a voltage measured from first electrode to second electrode is negative. Such polarity switching circuitry would be readily understood by a worker skilled in the art.

In further embodiments, switch 730 is a multi-state control device such as a potentiostat or a multi-position switch that allows the user to select various different states of visible light transmittance for the variable transmittance optical filter 750. For example, the user could select an intermediate state to indicate that a state part way between fully dark and fully light is desired. Power control electronics 740 can then apply the voltage to the variable transmittance optical filter 750 for a sufficient duration to achieve this intermediate state. A timer circuit or waveform generator or other electronics may be used for application of voltage for a controllable period of time, as would be readily understood by a worker skilled in the art. Other methods of causing the variable transmittance optical filters of the invention to reach an intermediate state, such as applying a reduced amount of voltage, may also be possible.

In some embodiments, power control electronics 740 can also include a voltage or current sensor, or an optical sensor, that can sense when the transition from one state of visible light transmittance to another is completed in the variable transmittance optical filter 750. For example, when the variable transmittance optical filter with an SC electrode system comprises a hybrid P/E switching material, when power control electronics 740 sense that the transition process is completed, it will open switch 730 in order to conserve power. Other functions and features that can be built into power control electronics 740 are also contemplated.

Control electronics 740 can also include electronic circuitry to apply an alternating waveform to the variable transmittance optical filter 750 instead of a constant DC voltage. The waveform can be in the form of a square wave, a sawtooth wave, a sinusoidal wave, or some other waveform. The amplitude of the wave may vary. An alternating waveform may be advantageous for some embodiments, by enabling a faster switching time and/or a longer product lifetime. In some embodiments, the potential difference applied between the two electrodes may be described as a square wave alternating between a first voltage and a second voltage, each of the first and second voltages being predetermined positive, negative, or zero with respect to ground. A square wave may be implemented by periodically switching the polarity of the voltage applied to the electrodes, for example. In one embodiment, a waveform can be applied to the interdigitated electrodes of the optical filter 750 by control electronics 740. In one embodiment, the waveform is a square wave, and an electrode potential difference between a first electrode and a second electrode can vary between about −2 Volts to about +2 Volts.

In another embodiment, the waveform, as measured with respect to ground at a first electrode, varies from 0 Volts to a positive voltage, and the waveform, as measured with respect to ground at a second electrode, varies from 0 Volts to a negative voltage. In another embodiment, the waveform, as measured with respect to ground or another reference level at either a first or a second electrode, varies from about 0 Volts to about 2 Volts; and in some embodiments, these two waveforms may be out of phase with each other such that the potential difference measured between the two electrodes is nonzero. In one embodiment, the frequency of the waveform is 100 Hz, or from about 0.1 Hz to about 1,000 Hz, or from about 0.001 Hz to about 100 KHz, or any amount or range therebetween.

In embodiments wherein the variable transmittance optical filter comprises multiple pairs of electrodes located in different regions, the control circuit may be configured to selectably apply the same voltages or different voltages, at the same or different times, to different pairs of electrodes. This may facilitate regional control over variable transmittance in different regions of the variable transmittance optical filter.

4. Additional Components of the Variable Transmittance Optical Filter

The variable transmittance optical filter with an SC electrode system may comprise one or more UV blockers to block some or a substantial amount of the UV light that the variable transmittance optical filter of the invention is exposed to in order to counteract UV light-induced degradation of the transition material. For example, in some embodiments where the variable transmittance optical filter of the invention comprises a hybrid P/E switching material, the variable transmittance filter requires UV radiation in order to transition to its dark state, however, as is appreciated by persons of skill in the art, chromophores, particularly organic ones, can degrade in UV light. To counter the UV light-induced degradation of the chromophores, one or more UV blockers can be used to block some or a substantial amount of the UV light that the variable transmittance optical filter of the invention is exposed to. The purpose of the UV blocker in these embodiments is to block a substantial amount of the UV light from reaching the transition material while allowing sufficient levels of UV radiation exposure to effect autodarkening. Variable transmittance optical filters comprising a transition material that is a liquid crystal material or suspended particle material may also benefit from the inclusion of one or more UV blockers. In contrast, when the variable transmittance optical filter comprises a transition material that is an inorganic material such as an inorganic electrochromic material, UV blocker may be less important.

The UV blocker may be incorporated in the substrate or applied as a layer on the substrate so as to block the transition material of the variable transmittance from the UV light. If the UV blocker is present as a UV blocking layer on the variable transmittance optical filter, it may comprise a film or layer of inorganic material, organic material or a combination of the two. Examples of inorganic materials are titanium dioxide, zinc oxide, cadmium oxide, tungsten trioxide, or a combination thereof. An inorganic UV blocking layer can be applied to the substrate by a variety of means such as chemical vapor deposition, physical vapor deposition, (e.g. sputtering, electron beam evaporation, and ion plating), plasma spray techniques or sol-gel processes. A UV blocker can be provided by a stack of thin film materials, (dichroic stack), with thickness and index of refraction chosen so as to reflect or absorb UV light. A UV blocker may be made up of a layer of polymer material that is inherently absorbing of the wavelength of light of interest or contains light absorber or stabilizer materials mixed, (dissolved or interspersed) into the polymer material or covalently bonded to the polymer itself. Examples of polymer materials include polyethylenes, polypropylenes, polybutylenes, epoxies, acrylics, urethanes, vinyls including polyvinyl chloride, poly(vinyl butyral)s, poly(vinyl alcohol)s, acetates, polystyrenes, polyimides, polyamides, fluorocarbon polymers, polyesters, polycarbonates, poly(methyl methacrylate), poly(ethyl methacrylate), poly(vinyl acetate), co-polymers of the aforementioned, and polymer blends of the aforementioned polymers.

A large number of light absorbers and/or stabilizer materials are known in the art and particularly useful ones include benzotriazoles, benzophenones, cyanoacrylates, hindered amines, oxalanilides and substituted triazines.

In embodiments where the variable transmittance optical filter with an SC electrode system comprises a hybrid P/E switching material, the concentration of UV light absorbers in the UV blocking layer and/or the thickness of the UV blocking layer are chosen so as to provide stability against sunlight degradation of the transition material layer beyond the UV blocking layer(s), while allowing sufficient levels of UV light exposure to effect auto-darkening. In one embodiment, the UV blocking film blocks more of the UV light below a certain wavelength. The UV blocking film blocks out the damaging high-energy UV at lower wavelengths, while allowing more of the lower energy UV light to pass through. The lower-energy UV light can be used to cause the auto-darkening. In one embodiment, the UV blocking film blocks most of the UV light below about 350 nm, but allows UV light between 350 nm to 400 nm to pass through. Examples of UV absorbing films that may be used in such embodiments include (EnergyFilm™ (described in WO2002/018132) and EnerLogic™ (described in WO2009/087575). Examples of UV blocking layers include optical clear pressure sensitive adhesives with UV blocking components (e.g. 8172PCL from 3M) that may be used to affix a variable transmittance optical filter to a surface.

Other coatings or materials that may be applied to a variable transmittance optical filter according to various embodiments include an anti-abrasion layer, an anti-reflective layer, an infra-red reflective layer, UV reflective layer, UV absorbing layer, hydrophobic coating layer, hydrophilic coating layer, self-cleaning coating layer or the like. The UV blocker may block most of the UV light below about 350 nm, or below about 365 nm, or below about 375 nm, or below about 380 nm, or below about 385 nm. In some embodiments, the UV blocker is a component of a substrate; for example, PET, with a UV blocking component (e.g. XST6578 from DuPont Teijin).

In some embodiments, the variable transmittance optical filter according to various embodiments of the invention may be disposed upon a pane of glass or other transparent material suitable for use as a window ("window material"), or incorporated into an insulated glazing unit (IGU), or a storm window, insert window or secondary glazing. Methods of making IGU, windows or the like and affixing an optical filter to glass or other suitable materials are described in the art. The optical filters may be applied to the window material using an optically clear adhesive; in other embodiments the second layer comprising the transition material may first be applied to the window material, and the first layer comprising the first substantially transparent substrate with the SC electrode system disposed thereon applied to the second layer, thereby assembling the variable transmittance optical filter directly on the window material. The window material with optical filter may subsequently be used in assembly of an IGU according to known methods.

In some embodiments, the variable transmittance optical filter comprising a hybrid P/E switching material has a low power requirement, making it particularly suitable for mobile devices (e.g. those not coupled to a conventional AC power supply), such as automotive glass applications, adjustable mirrors, auto-darkening sunroofs or the like, or opthalmic devices.

The variable transmittance optical filter comprises a SC electrode system that is in contact with the hybrid P/E switching material. The electrodes of the SC electrode system are disposed on the surface of the same substantially transparent substrate. Leads are connected to each electrode in order to apply a voltage to the hybrid P/E switching material. When an electric voltage is applied to the hybrid P/E switching material when it is in its dark state, the switching material lightens and transmits a greater percentage of incident visible light until it reaches a light state. Control electronics allow a user to control when and how much voltage to apply to the filter. In this manner, the components of the optical filter of the present invention provide for an optical filter that can be in a light state or a dark state, that can automatically go into its dark state when exposed to UV light from the sun but can be switched back to a lighter state through application of an electric voltage when desired.

Embodiments of the invention include optical filters that can also reduce transmission of light in the UV portion of the spectrum. In one embodiment, UV light transmittance of the optical filter of the invention is less than 30%. In another embodiment of the invention, the UV light transmittance of the optical filter is less than 20%. In a further embodiment of the invention, the UV light transmittance of the optical filter is less than 10%. In another embodiment of the invention, the UV light transmittance of the optical filter is less than 5%. As discussed, minimal electric voltage is required and only to effect lightening of the variable transmittance optical filter comprising a hybrid P/E switching material of the invention. Maintaining the optical filter in a stable state does not require constant application of voltage.

Rather, any lightening required to adjust for auto-darkening, when in the presence of UV or solar radiation, can be made by intermittent application of voltage to maintain a constant light state, or by applying a reduced amount of voltage. In this way, the amount of power consumed by the optical filter is minimized. In addition, the minimal voltage) requirements of the optical filters of the invention make them amenable to sheet materials having a wide range of sheet resistances as described herein. Thus, optical filters of the present invention are amenable to interdigitated electrodes made from conductive material having sheet resistances ranging between about 1 Ohms/square to about 10,000,000 Ohms/square, or any amount or range therebetween, including those exemplified herein.

Process for Preparing the Variable Transmittance Optical Filter

The variable transmittance optical filters described herein are suitable for manufacturing switchable windows, for example, "smart" windows with fewer components. By forming interdigitated first and second electrodes onto one transparent conductive substrate, a second substrate comprising a conductive layer used in "smart" window applications may not be required. Thus, in some embodiments of the variable transmittance optical filter, a second transparent conductive substrate is replaced with a much lower cost nonconductive substrate.

In some embodiments, a bus bar can be applied to one edge of a substrate in order to provide an electrical connection. Bus bars can be formed from a conducting material such as copper, aluminum, silver, gold, or other conductive materials. A bus bar can be printed on using for example a silver epoxy or silver ink material. A bus bar can also be formed using copper tape with conductive adhesive. Electrical leads can be attached to the bus bar.

The variable transmittance optical filters may be prepared according to methods known in the art. For example, roll-to-roll processing methods can be used for making the variable transmittance optical filter. Roll-to-roll methods may be particularly suited to production of flexible optical filters in the form of films, for example. Such methods generally comprise the steps of a) providing a flexible substantially transparent substrate, b) disposing a transparent conductive material on one side of the flexible transparent substrate, c) forming the SC electrode system in the transparent conducting material, and d) disposing the transition material in contact with the SC electrode system. In embodiments where the variable transmittance optical filter comprises a first and third layer, the method further comprises the step of e) providing a second flexible substrate on top of the transition material; forming a "sandwich" structure with the transition material in contact with the SC electrode system and the two substantially transparent substrates. Where the substrate including a transparent conductive layer is available, the step of b) disposing a transparent conductive material may be forgone, and the method may proceed with the step c) of forming the SC electrode system thereon. Similarly, where the substrate is available "pre-printed" with an SC electrode system, the step c) of forming the SC electrode system may be forgone, and the method may proceed with the step d) of disposing the transition material thereon.

In some embodiments where the transition material is a hybrid P/E switching material, the formulation comprising same may have a viscosity at room temperature that is too viscous to be readily applied, thus the formulation may be made into a lower-viscosity liquid by heating to allow it to be applied or coated onto the substrates. For example, the switching material may be heated to a temperature of about 60° C. to about 80° C. and pressed between the first substrate and optional third substrate. In some embodiments, the formulation may further comprise a co-solvent to facilitate coating in a roll-to-roll processing method, allowing the switching material to be cast as a liquid and then further treated to increase the viscosity of the material to form a gel. For example, the hybrid P/E transition material can be dried wherein the solvent and/or co-solvent is evaporated from the hybrid P/E switching material. In other embodiments, the hybrid P/E switching material may comprise one or more component that can be cross-linked and/or polymerized, and cured to increase the viscosity, and/or to form a gel. Curing the hybrid photochromic/electrochromic transition material may be accomplished, for example, with UV light. A photoinitiator may be added to the switchable material which, when exposed to UV light, can help to cross-link the formulation to increase its viscosity. Other methods of curing such as with heat or exposure to electron beams may be possible with different formulations. One skilled in the art will appreciate that this polymerization and/or crosslinking can be initiated by chemical-, thermal-, or photo-type initiators. A common method of UV curing can be accomplished by adding a constituent that, when exposed to UV light, will form a radical to initiate polymerization and/or cross-linking. Suitable polymerization initiators are known in the art and include, for example, heat sensitive initiators such as AIBN, photo-initiators such as DAROCUR 4265. The gelled hybrid photochromic/electrochromic transition material can then adhere to both substrates to form an integral structure.

Once the filter has been made, it can be cut to size, sealed around the perimeter if necessary, and an electrical connection can be made to the electrodes. The electrical connection can be made by printing bus bars onto the substrate in contact with the transparent conductive coating. Electrical leads can then be attached to the bus bars. The variable transmittance optical filter with the SC electrode system when completed will transition from one state of visible light transmittance to another when an appropriate electrical charge is applied to the electrodes.

Testing the Optical Filter

The performance efficacy of the variable transmittance optical filters with an SC electrode system according to the present invention can be tested to determine characteristics such as, for example, the amount of visible light transmittance, haze, switching speed, sheet resistance photostability, polarity cycling, and voltage requirements. These characteristics can be determined using standard techniques known in the art.

Clarity in optical filters can be caused by transmission haze due to cloudiness caused by scattering of light. Light may be scattered by particles that are suspended in the substance. Haze may be measured by methods known in the art, for example, using a "hazemeter" (e.g. XL-211 Hazegard, BYK Gardner), according to known and/or standardized methods. Optionally, the haze of the optical filters according to various embodiments is between about 0% and about 5%. In some embodiments of the invention, the optical filter has a haze transmission of about 5% or less, about 3% or less, about 2% or less, about 1.5% or less, or about 1% or less; or from about 0 to about 2%, or from about 0.5% to about 3%, or any amount or range therebetween.

"Switching time" ("switching speed") refers to the time necessary for a material to transition from a dark state to a clear state, or from a clear state to a dark state, or to alter light transmission by a defined amount (e.g. 60% to 10%

VLT in 5 minutes) Generally the optical filters of the present invention will have a darkening time of between about 1 second and 30 minutes to reach about 10% of the VLT of the dark state from the lightened state, and a lightening time of between about 1 second and 30 minutes to reach about 90% of the VLT of the light state from the darkened state. In some embodiments of the invention, the darkening time and lightening time of the optical filter may independently be from about 0.5 minutes (30 seconds) to about 5 minutes, or any amount or range therebetween, for example 0.5, 1, 1.5, 2, 2.5, 3, 3.5, 4, 4.5 or 5 minutes, or any amount of time or range therebetween.

In some embodiments where the variable transmittance optical filter with an SC electrode system according to the present invention comprises a hybrid P/E switching material, the switching of the hybrid P/E switching material from the dark state to the light state over the electrode connected to the positive potential (anode) progresses more rapidly than the switching of the transition material from the dark state to the light state over the electrode connected to the negative potential (cathode).

In some embodiments, where the variable transmittance optical filter with an SC electrode system according to the present invention comprises a hybrid P/E switching material, and the polarities of the applied voltage is switched, the hybrid P/E switching material over the electrode connected to the negative potential completes the transition from the dark state to the light state within 30 minutes, or within 10 minutes, or within 5 minutes, or within 3 minutes, or within 1 minute, or within 30 seconds of reversing the polarity of the voltage.

Uses of the Variable Transmittance Optical Filter

The variable transmittance optical filters of the present invention can be incorporated into a variety of applications, including devices or systems where it is desirable to dynamically control and filter light. The variable transmittance optical filters comprising first and second layers may applied or laminated onto another substrate. Exemplary applications include architectural windows, vehicle (automobile, bus, train, plane, boat, ship or the like) windows, windscreens or visors, ophthalmic devices and the like. It is also contemplated that in some embodiments different regions of such architectural windows, automotive windows, and ophthalmic devices can be controlled individually, or in groups, by designing the variable transmittance to include multiple pairs of electrodes that can be individual controlled.

1. Variable Transmittance Windows

Variable transmittance optical filters of the present invention can be incorporated into a variety of window systems such as, for example, architectural smart window systems, or automotive window systems, to confer controllable variable transmittance functionality on the window system. As described herein, the variable transmittance optical filter with the SC electrode system according to the invention can be made with a first layer and optionally a third layer that comprises rigid or flexible, substantially transparent substrate(s). When the variable transmittance optical filter is prepared with one or two rigid substantially transparent substrates, the variable transmittance optical filter can be directly incorporated into the structure of the window system. Alternatively, when the variable transmittance optical filter is prepared with one or two flexible substantially transparent substrates, the variable transmittance optical filter can be laminated onto a rigid substantially transparent substrate that is incorporated into the window system. The rigid transparent substrate may be flat, or curved (e.g. a curved window). Electrical leads are connected to the SC electrode system of the variable transmittance optical filter. The electrodes are in contact with the transition material of the variable transmittance optical filter and when a voltage is applied to the electrodes the transition material transitions from one state of visible light transmittance to another. Such window systems, when comprising a hybrid P/E material will darken when exposed to UV or sunlight, and lighten when an electric voltage is applied. The controlled reduction of the VLT of the window may be useful by reducing glare, and/or reducing solar heat gain, and/or improve occupant comfort.

A variable transmittance window for a vehicle may have a relative dark tint even in the light state—a dark tint may be beneficial for reducing solar heat gain inside the vehicle, improve fuel efficiency by reducing a user's need for air conditioning, and/or provide visual privacy. In one embodiment, a variable transmittance window for a vehicle may have a VLT from about 0% to about 20% in the dark state, or any range or amount therebetween, for example 0, 1, 2, 3, 4, 5, 6, 7, 8, 9, 10, 11, 12, 13, 14, 15, 16, 17, 18, 19 or 20%; and from about 5% to about 30% in the light state, or any range or amount therebetween, for example 5, 6, 7, 8, 9, 10, 11, 12, 13, 14, 15, 16, 17, 18, 19, 20, 21, 22, 23, 24, 25, 26, 27, 28, 2 or 30%. In some embodiments, the vehicle window may have dark and light state VLTs with a contrast ratio of at least 2:1, 3:1, 4:1, 5:1 or any amount or range therebetween.

Two or more variable transmittance windows in a vehicle may have the same, or different VLT in light and dark states, and/or same or different contrast ratios. For example, a vehicle may have a sunroof with about 5% VLT in a dark state and about 15% in a light state (~3:1 contrast ratio), while a side or rear window may have about 15% VLT in a dark state and about 60% VLT in a light state (~4:1 contrast ratio). Greater VLT and/or a higher contrast ratio may provide increased visibility. This may be desirable to provide vehicle passengers with a better view outside. For front (windshield) and side-front windows where driver visibility is of greater importance, a variable transmittance window with greater VLT than is used in the rest of the vehicle windows may be selected. In one embodiment, front side window has a visible light transmittance of 20% in the dark state and 80% in the light state. In some embodiments, a portion of the window of the vehicle may comprise a portion that has variable transmittance. For example a top portion of a front window may comprise a variable transmittance optical filter that darkens with exposure to sunlight, and may be cleared automatically with application of a voltage when a light sensor indicates reduced light outside, or in response to a drivers preference by activation of a switch to initiate application of a voltage. For a vehicle with multiple variable transmittance windows, each window may be independently controlled, or the multiple windows may be simultaneously controlled as a group via a control system.

The substrate for a variable transmittance window for a vehicle may be tempered glass, polycarbonate, acrylic or the like. A variable transmittance window for a vehicle comprise a variable transmittance optical filter \ comprising a transition material and an SC electrode system. The transition material may comprise a hybrid P/E compound. The variable transmittance window may further comprise a power source, such as an energy harvesting power source, and an electrical system configured to receive power from the power source and to provide a voltage to a first electrode and a second electrode of the variable transmittance optical filter. The variable transmittance window may further comprise a frame, such as a generally C-shaped gasket surrounding the periphery of the window. Electrical system and power sources, including energy harvesting power sources as described herein may be used in the variable transmittance window. A variable transmittance optical filter may be laminated to one side of the window using an adhesive, such as 8172 PCL, as described herein. Alternately, a variable transmittance optical filter may be laminated between two substrates with PVB or EVA interlayers, as described above.

The variable transmittance window may automatically darken when exposed to UV light (for embodiment where the switching material is a hybrid P/E switching material). Activation of a switch (e.g. by control electronics or by a user) applies power from the power source to the first and second electrodes of the variable transmittance window and fades the window. Windows with variable tinting may be advantageous in that it reduces solar heat gain inside the vehicle, and reduces glare, but can be faded where more light or visibility through the window is desired. A variable tint window may eliminate the need for an opaque blind to block off the sunroof.

2. Variable Transmittance Ophthalmic Device

Variable transmittance optical filters of the present invention can be incorporated as a variable transmittance lens in a variety of ophthalmic devices. Variable transmittance ophthalmic devices of the invention will transition from one state of visible light transmittance to another with the application of an electric charge. In some embodiments, where the variable transmittance optical filter comprises a hybrid photochromic/electrochromic, the variable transmittance ophthalmic devices will darken automatically when exposed to UV or in sunlight and will lighten through application of an electric charge. For example, the variable transmittance optical filters of the invention can be incorporated as a variable transmittance lens in sunglasses, sports eyewear such as ski goggles and cycling glasses, industrial uses such as safety eyewear, and others.

The variable transmittance optical filter according to various embodiments of the invention can be incorporated into ophthalmic devices in a variety of ways. A flat lens may incorporate an optical filter by application of a variable transmission optical filter comprising a flexible substrate to a surface of the lens material (e.g. the lens material may comprise the optional third layer of some embodiments as described herein). A curved or spherical lens may incorporate an optical filter. Such a lens may comprise a first substrate that is molded, cast, vacuum formed, or thermoformed into a suitable shape, according to known methods. A layer of conductive material may be coated onto the formed first substrate, and an SC electrode system of suitable layout etched into the conductive material. A layer of transition material may be subsequently applied, followed by lamination or adherence of a second substrate shaped to complement the first substrate and transition material may be applied and sealed as necessary; connectors for connecting bus bars, electrodes and the like to a control system may be subsequently applied. The SC electrode system may comprise any suitable layout—a circumferential layout of first and second electrodes is illustrated in FIG. 9 for the lens of goggles of FIG. 10.

Figure 9:
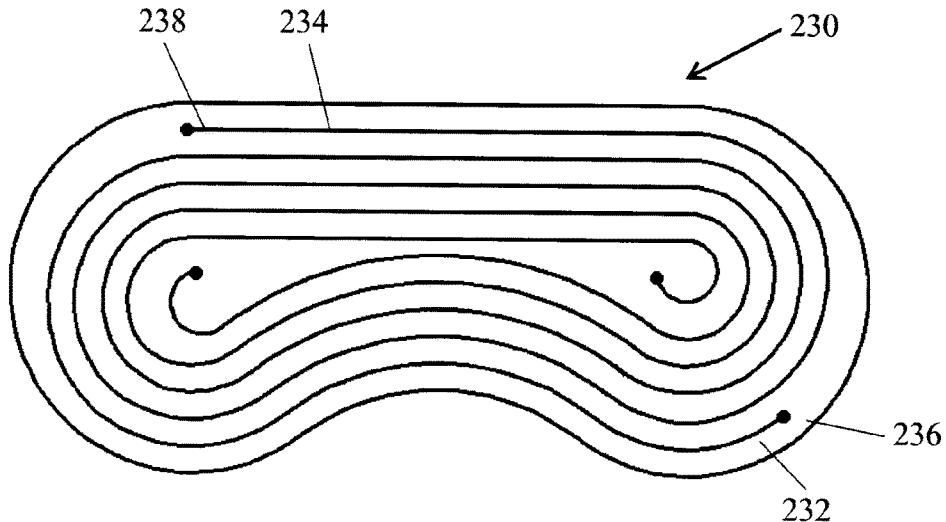
FIG. 9 illustrates a circumferential layout of electrode configuration, according to some embodiments of the invention.
Figure 10:
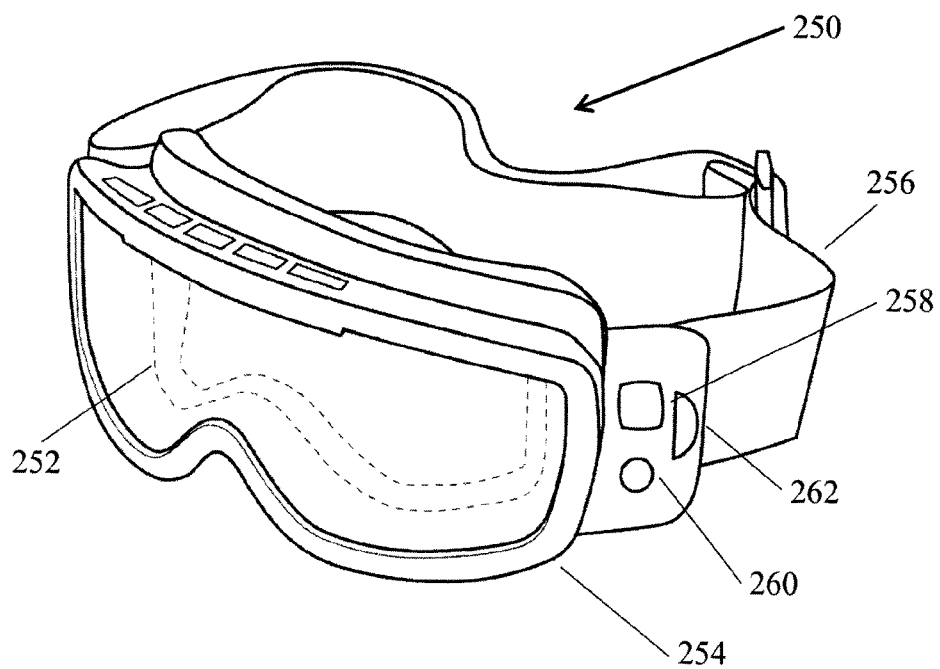
FIG. 10 shows an opthalmic device comprising a circumferential electrode layout as illustrated in FIG. 9, according to some embodiments of the invention.

Referring to FIG. 9, an SC electrode system according to another embodiment of the invention is shown generally at 230. First 232 and second 234 circumferential electrodes follow a coiling path generally conforming to the shape of the substrate. For this embodiment, the variable transmittance may be cut to a suitable lens shape, for incorporation into an opthalmic device, such as that illustrated in FIG. 10. Contact points 236, 238 at electrode ends may connect the lens to leads (not shown) connected to an electrical system to provide voltage to be applied to the first and second electrodes. Referring to FIG. 10, an opthalmic device according to various embodiments of the invention is shown generally at 250. A variable transmittance lens 252 comprising first and second electrodes of an SC electrode system is held in a frame 254, the frame configured to position the lens 252 in front of the eyes when in use. A strap 256 may hold the opthalmic device on a user's head when in use. A compartment in the frame 254 contains a power source 258. To operate the device, a user may depress a button 260 to close a switch of the control electronics 262 of an electrical system comprising a portion of the SC electrode system and provide a voltage from the power source 258 to the first and second electrodes, and the variable transmittance optical filter transitions from a dark state to a faded state.

Embodiments of the invention are illustrated, in part, by the following non-limiting methods and examples:

EXAMPLES

Example 1: Preparation of Selected Hybrid P/E Compounds

S001 and S002 were Prepared as Described in U.S. Pat. No. 7,777,055.

Synthesis of S042—

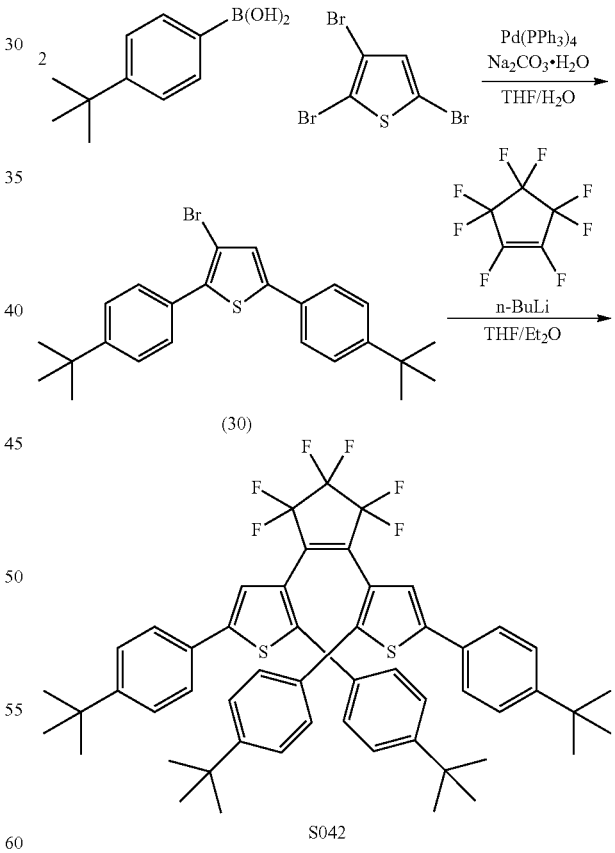

(30)

S042

Synthesis of 3-bromo-2,5-bis(4-(tert-butyl)phenyl) thiophene: (30)

Sodium carbonate monohydrate (58.0 g, 468 mmol) was dissolved in water (500 mL) and a solution of 4-(tert-butyl)- phenylboronic acid (40.0 g) and 2,3,5-tribromothiophene (30.0 g, 94 mmol) in THF (500 mL) was added, and deoxygenated by bubbling with argon. Pd(PPh$_3$)$_4$ (5.0 g, 4.30 mmol) was added and the mixture refluxed for 24 h. The mixture was cooled and the aqueous phase separated and extracted with EtOAc. Organic fractions were combined washed with water (500 mL) and dried over MgSO$_4$. The solvent was evaporated and the crude product washed in MeOH, filtered and dried overnight to afford a light yellow, powdery solid (35.46 g, 89%).

Synthesis of S042 (3,3'-(perfluorocyclopent-1-ene-1,2-diyl)bis(2,5-bis(4-(tert-butyl)phenyl)thiophene.)

A solution of (30) in anhydrous THF/ether cooled to −45° C. and treated with nBu-Li (2.5 M in hexanes, 35 mL, 87 mmol) dropwise under a n argon atmosphere. The reaction mixture was stirred for a further 15 minutes followed by addition of octafluorocyclopentene (5.6 mL, 41.5 mmol) using a cooled gas tight syringe. The reaction was allowed to stir until the temperature reached −10° C., quenched by the addition of 10% HCl (50 mL). The aqueous layer was separated and extracted with ether. The organic phases were separated and pooled, dried over MgSO$_4$, filtered and solvent removed by rotary evaporation. The crude product was stirred in MeOH for 3 hours, and the resulting precipitate filtered, dried and purified using flash chromatography (hexanes), affording 2 fractions—F1 was pure S006 (TLC), F2 contained S006 along with a fluorescent byproduct by TLC. F1, 5.35 g, 14.8%) and F2, 10.4 g (~75% pure, 22%) as light yellow, powdery solids. $^1$H NMR (400 MHz, CDCl$_3$) δ 7.37 (d, J=8.5 Hz, 4H), 7.30 (d, J=8.5 Hz, 4H), 7.05 (d, J=8.4 Hz, 4H), 6.92 (d, J=8.4 Hz, 4H), 6.13 (s, 2H), 1.34 (s, 18H), 0.91 (s, 18H).

Synthesis of S054—3,3'-(perfluorocyclopent-1-ene-1,2-diyl)bis(2,5-bis(4-methoxyphenyl)thiophene)

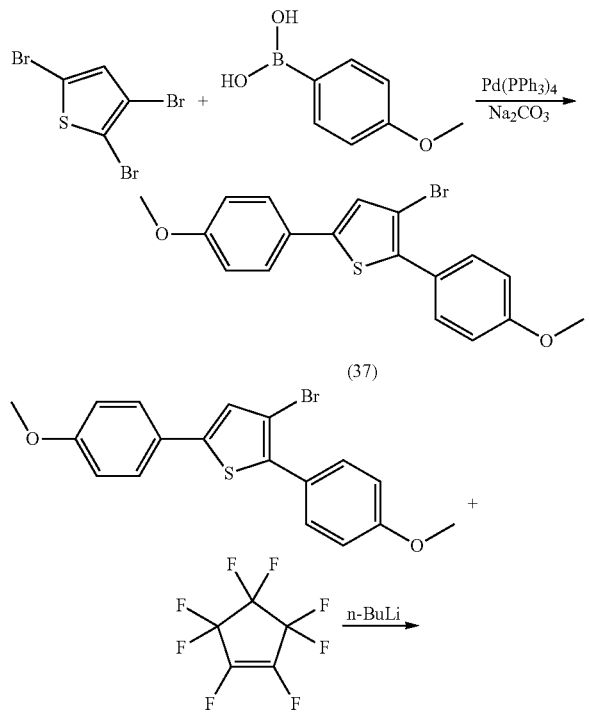

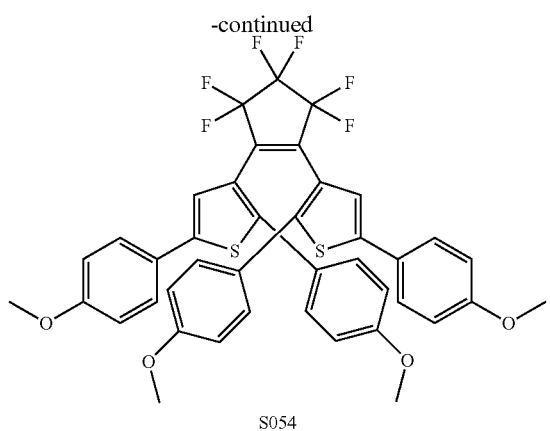

S054

Synthesis of 3-bromo-2,5-bis(4-methoxyphenyl)thiophene (37)

2,3,5-Tribromothiophene (6.42 g, 20 mmol), 4-methoxyphenylboronic acid (6.38 g, 42 mmol) and sodium carbonate (8.5 g, 80 mmol) were stirred in THF/water mixture (125/50 ml) for 90 min at RT under argon flushing. Pd(PPh$_3$)$_4$ (693 mg, 0.6 mmol) was added. The mixture was refluxed for 16 h (TLC), cooled to RT and THF was removed by evaporation. Water was added and aqueous fractions extracted with EtOAc. The organic fractions were combined, solvent removed and the crude product purified by flash chromatography (Silica gel; hexane/chloroform/EtOAc; gradient up to 20% chloroform then 20% EtOAc) to yield 3-bromo-2,5-bis(4-methoxyphenyl)thiophene (4.9 g, 13 mmol, 65%).

Synthesis of S054: Compound (37)

(10.64 g; 28.4 mmol) was dissolved in anhydrous ether (350 mL) and cooled to −25° C. n-BuLi (14.2 mL; 35.5 mmol; 2.5 M in hexane) was added. The mixture was stirred at this temperature for 0.5 h. Octafluorocyclopentene (1.9 mL; 14.2 mmol) was added in two portions, and the reaction was allowed to warm slowly over 3 h. The reaction was quenched by addition of 10% aqueous HCl (50 mL). Organic layer was separated and the aqueous was extracted with EtOAc (250 mL). Solvent from the combined organic extracts was evaporated and crude material was purified by column chromatography (Silica gel; hexanes/EtOAc up to 30%). Collected product was sonicated in methanol and pale yellow powder was filtered and dried in air (4.46 g; 5.82 mmol; yield 41%). $^1$H NMR (400 MHz, CDCl$_3$) δ 7.32 (d, J=8.7 Hz, 4H), 6.91 (dd, J=8.7, 2.4 Hz, 9H), 6.60 (d, J=8.6 Hz, 4H), 6.25 (s, 2H), 3.85 (s, 6H), 3.41 (s, 6H).

Synthesis of S068—12,12'((4,4'-(perfluorocyclopent-1-ene-1,2-diyl)bis(5-(4-(tert-butyl)phenyl)thiophene-4,2-diyl))bis(4,1-phenylene))bis(12-methyl-2,5,8,11-tetraoxatridecane)

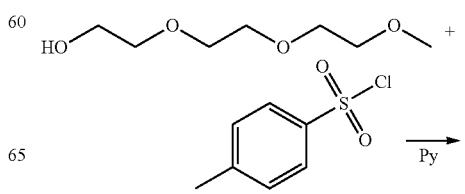

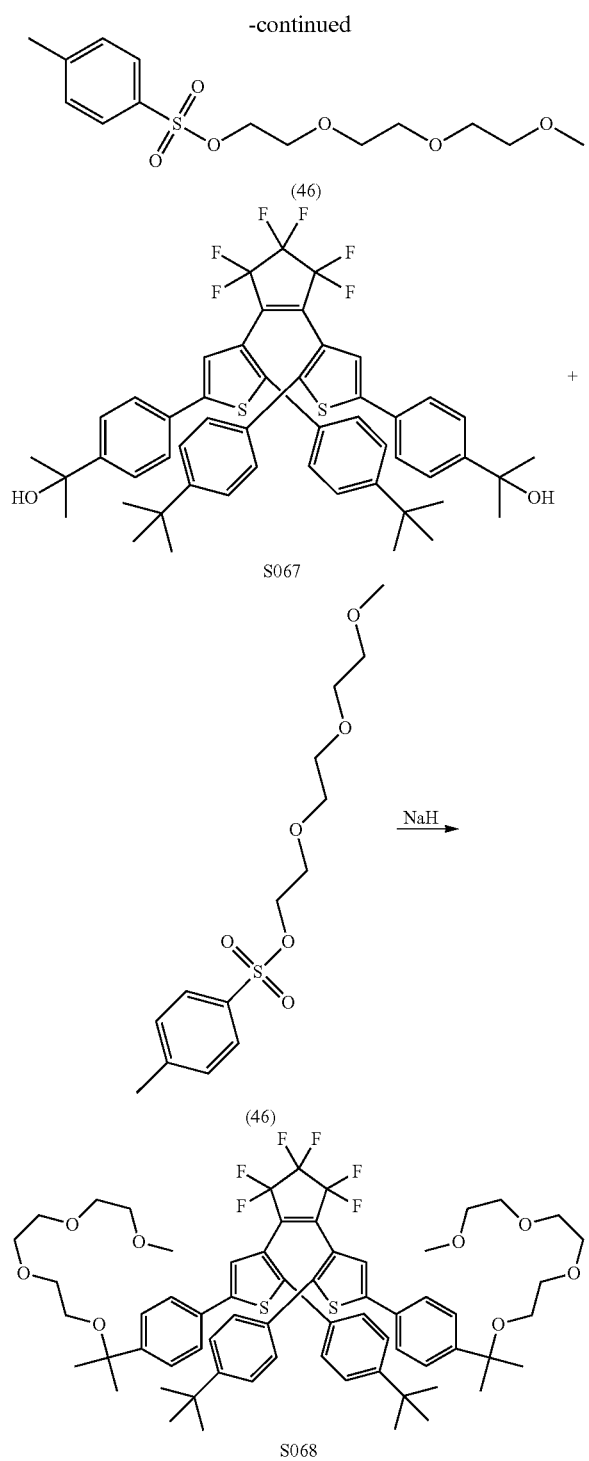

Synthesis of 2-(2-(2-methoxyethoxy)ethoxy)ethyl 4-methylbenzene sulfonate (46)

To a solution of p-toluenesulfonyl chloride (3.17 g, 19.3 mmol) in 20 mL of pyridine was added 2-(2-(2-methoxyethoxy)ethoxy)ethanol (4 g, 21 mmol), stirred at 0° C. for 12 h and at RT for 2 h. To this suspension, water and hexanes and ethyl acetate were added and separated. The organic layer was neutralized with dilute HCl and separated again; organic fractions were pooled, dried (MgSO$_4$ and NaHCO$_3$), filtered, and concentrated under reduced pressure to give 4.87 g, 15.3 mmol (79%) of 2-(2-(2-methoxyethoxy) ethoxy)-ethyl 4-methylbenzene sulfonate as a colorless oil.

Synthesis of S068

Sodium hydride (0.24 g, 6 mmol, 60% dispersion in oil) was washed with hexanes (6 mL) and a solution of di-alcohol S067 (1.33 g, 1.52 mmol) in THF (25 mL) was added under argon. The reaction mixture was stirred for 1 h at RT. To the resulting suspension was added a solution of (46) (1.06 g, 3.35 mmol) in anhydrous dimethylformamide (12 mL) in one portion and the mixture was stirred for 48 h. The reaction was quenched by addition of brine (100 mL) and extracted with EtOAc (3×100 mL). The organics were combined, washed with water (2×100 mL), dried over MgSO$_4$, filtered and evaporated to dryness. The residue was purified by column chromatography (Silica gel; hexane/EtOAc (50/50) as the eluent to obtain 1.24 g (1.06 mmol; 70%). $^1$H NMR (400 MHz, CDCl$_3$) δ 7.44 (d, J=8.4 Hz, 4H), 7.36 (d, J=8.4 Hz, 4H), 7.09 (d, J=8.4 Hz, 4H), 6.96 (d, J=8.3 Hz, 4H), 6.21 (s, 2H), 3.72-3.68 (m, 12H), 3.66 (t, J=5.3 Hz, 5H), 3.61-3.57 (m, 4H), 3.43-3.37 (m, 10H), 1.58 (s, 12H), 0.95 (s, 18H).

Example 2: Preparation and Testing of Variable Transmittance Optical Filters with an Interdigitated SC Electrode System Comprising Symmetric Electrode Widths Six variable transmittance optical filters comprising different interdigitated SC electrode systems were prepared as follows. A test wafer was formed from a piece of ITO-coated glass purchased from Delta Technologies (Stillwater, Minn.). Areas with symmetric interdigitated electrodes were created in which both first and second electrodes and bus bars were of equal size, with spacing and electrode digit width as indicated in Table 1. A photoresist layout of the electrode patterns was created with CAD, a suitable photomask produced and the pattern wet-etched into the ITO coating using standard photolithographic techniques. Briefly, the substrate was cleaned with acetone and isopropyl alcohol, and AZ™ MIR™ 703 resist spincoated at 4000 rpm and baked at 90° C. for 60 seconds (following manufacturer's instructions). The electrode patterns were exposed through the photomask (chrome on glass), and the substrate baked again at 110° C. for 60 seconds. The substrate was then developed in AZ™ MIF™ 300 for 60 seconds, and etched for 4.5 minutes in 37% HCl, and rinsed to remove etchant. Remaining resist was removed with acetone.

TABLE 1

| SC Electrode device numbers and dimensions of symmetric electrodes | | |
|---|---|---|
| Device # | Spacing A (mm) | Digit width B (mm) |
| 1 | 0.5 | 1 |
| 2 | 0.25 | 0.5 |
| 3 | 0.1 | 0.1 |
| 4 | 0.05 | 0.05 |
| 5 | 0.025 | 0.025 |
| 6 | 0.015 | 0.015 |

To construct the SC electrode devices, a hybrid P/E switching material (according to Formulation 9—see Example 4) was then added. A drop of formulation was placed on the device to be tested and a small glass cover slip was placed he formulation distributed to a uniform layer with application of the cover slipon top of each one of the interdigitated patterns and a plain glass slide (a second substrate) was added on top to form the variable transmittance optical filter. The switching material was darkened with UV light for 1 minute, and then bleached with electricity by applying approximate two volts DC across the two electrodes of the SC electrode system via the bus bars for approximately 30 seconds to five minutes by electrical leads from a power source to the bus bars of the electrodes.

All of devices 1-6 demonstrated successful electrofading of the switching material, however improved uniformity of fading of the devices was observed in devices with narrower electrodes. Devices 1 and 2 demonstrated electrofading initially over the anode, such that the interdigitated electrode pattern was highlighted by the lighter and darker portions of the hybrid P/E switching material. Device 3 demonstrated electrofading over the anode and mostly over the cathodes, although some faint lines of darkened material were still visible over the cathode. In devices 4, 5, and 6, fading was more uniform Example 3: Preparation and Testing of Variable Transmittance Optical Filters with an SC Electrode System Comprising Asymmetric Electrode Widths This example describes the preparation and testing of variable transmittance optical filters in which the SC electrode system of the variable transmittance optical system is patterned asymmetrically. A first electrode comprises fingers that are wider than those of the second electrode, providing a greater square area for the first electrode relative to the second electrode. In devices comprising a hybrid P/E switching material where the larger electrode is the anode (positive potential) and the smaller electrode is the cathode (negative potential), all, or substantially all, of the area of the device can be electrofaded. This example demonstrates that an asymmetric interdigitated electrode pattern can provide better uniformity while electrofading the switching material, with a smaller electrode area, and in some applications, a reduced need for etching thin electrodes.

Six devices were prepared as described for Example 2, with Formulation #9. Electrode configuration are set out for devices 7-12 in Table 2. Devices were exposed to UV light for 1 minute to darken the hybrid P/E formulation.

TABLE 2

SC Electrode devices and dimensions of asymmetric electrodes

| Device # | Spacing A (mm) | Digit width B1 (mm) | Digit Width B2 (mm) | B1/B2 % area |
|---|---|---|---|---|
| 7 | 0.05 | 1 | 0.05 | 90.9/4.5 |
| 8 | 0.05 | 1 | 0.5 | 64.5/32.25 |
| 9 | 0.05 | 1 | 0.1 | 86.9/8.7 |
| 10 | 0.05 | 1 | 0.2 | 80/16 |
| 11 | 0.05 | 1 | 0.3 | 74/22.2 |
| 12 | 0.03 | 1 | 0.03 | 94.3/1.06 |

Figure 11:
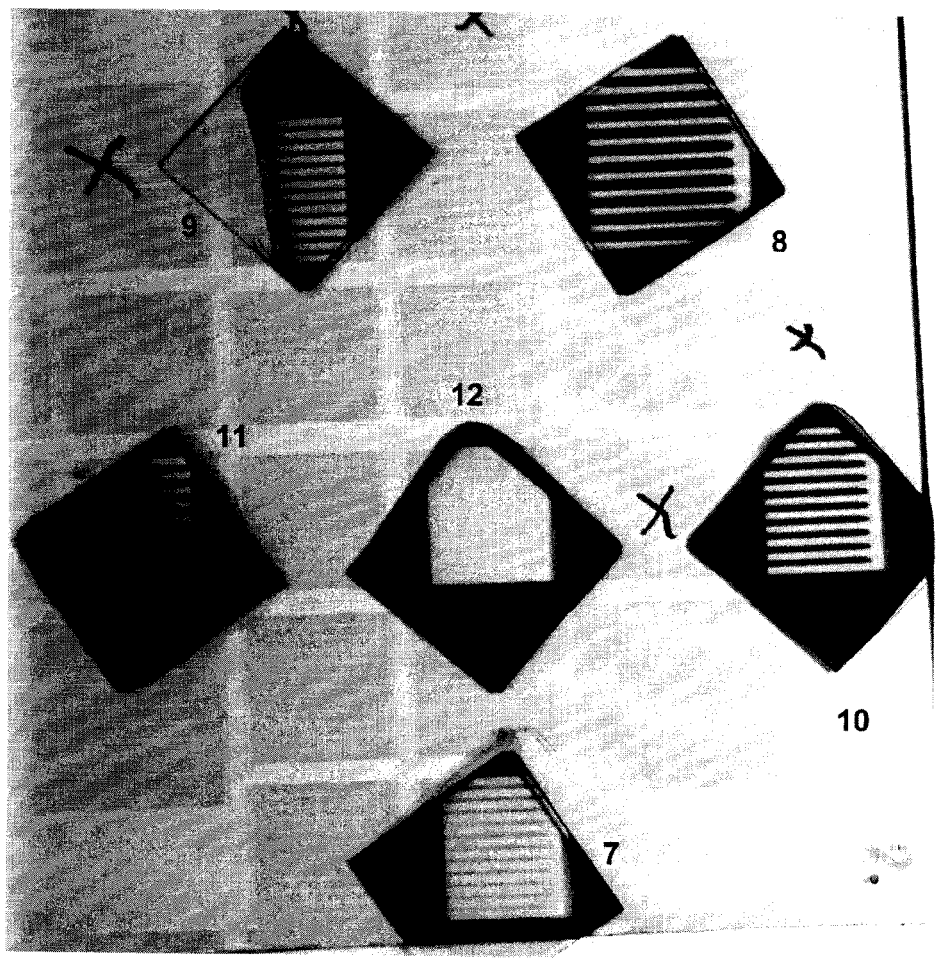
FIG. 11 shows a photograph of devices with asymmetric electrodes, according to some embodiments of the invention. Device numbers are indicated adjacent to the devices.

FIG. 11 is a photograph of devices 7-12, after electrofading of the UV-darkened devices for 30 seconds to 1 minute. Positive voltage was applied to the first electrode (1 mm digit width for all devices) and a negative voltage to the second (narrower) electrode cathode. Fading of the hybrid P/E switching material to a clear state occurred first over the anode electrode for all of devices 7-12. In the devices with a very thin cathode (e.g. device 12 and device 7), the fading spread over the entire device quickly to give good uniformity, and the devices were fully faded in about 20 seconds. Device 9 also demonstrated fading over the entire device but took longer for the fading to diffuse over the negative electrode. Device 10 and 11 did not completely fade over the negative electrode even after being left for more than one minute.

Example 4: Use of Alternating Voltages to Transition Optical Filter Devices Comprising Asymmetric Electrode Configurations This example demonstrates the use of alternating polarity of electrodes to improve transition (switching) time of a device comprising a hybrid P/E switching material. Devices 7-12 according to Example 2 were prepared as described. A positive voltage was applied to the larger first electrode (anode) and a negative voltage was applied to the narrower second electrode (cathode). The polarity was reversed once during the fading period such that a negative voltage was applied to the larger first electrode to make it the cathode and a positive voltage was applied to the narrower second electrode to make it the anode. Potential was applied at each polarity for about 15 to 30 seconds. Devices 7 and 8 were tested and both were completely faded to good uniformity without stripes in about 30 seconds to one minute by manually switching the polarity between one and three times during the fading.

Example 5: Preparation of the Hybrid P/E Switching Material

Table 3 sets out formulations for hybrid P/E switching material that may be used in device of the present working examples. Compounds that may be used in the formulations include those according to Formulae IA/IB, and those illustrated herein. In some examples, the compound used in a formulation may be S001, or a derivative thereof having a functional groups on one or more of the four peripheral thiophene rings; or S002, or a derivative thereof having a functional group on one or more of the peripheral phenyl rings; or S042, or a derivative thereof having another functional group on one or more of the peripheral phenyl rings; or S054, or a derivative thereof having another functional group on one or more of the peripheral phenyl rings; or S068, or a derivative thereof having a functional group on one or more of the peripheral phenyl rings.

PEGDMA, solvents, electrolytes, initiators, charge carriers, cosolvents, polymers and other formulation components are available from commercial suppliers (e.g. Sigma-Aldrich); or as indicated. DAROCUR™ is available from CIBA Specialty Chemicals of Basel Switzerland, a division of BASF. PVB B-90 is available from Butvar, a division of Solutia Inc. of St. Louis, Mo.

Formulation #2 was prepared for photostationary state (PSS) determination, using $2 \times 10^{-5}$ M of the indicated compound, in a solvent (triglyme).

TABLE 3

| Formulation component | Type of formulation component | Formulation (% wt of components) | | | | | | | |
|---|---|---|---|---|---|---|---|---|---|
| | | 1 | 3 | 4 | 5 | 6 | 7 | 8 | 9 |
| chromophore | | 3 | 3 | 5 | 3.4 | 3.4 | 2 | 0.5 | 5 |
| solvent | triglyme | 75 | 74 | 72 | 70.7 | 70.6 | 28.8 | 93.5 | |
| | cyclopentanone | | | | | | | | 89 |
| | tetraglyme | | | | | | | | |
| | GBL | | | | | | | | |
| electrolyte | LiClO4 | 1 | 1 | | | | | 1 | |
| | TBAPF6 | | | 1 | 1 | 1 | 0.4 | | 1 |
| polymer | PEGDMA860 | 15 | | | | | | | |
| | PMMA | | 15 | | | | | 5 | 5 |
| | PVB B90 | | | 22 | 24.9 | 25 | 8.8 | | |
| initiator | DAROCUR | 0.01 | | | | | | | |
| charge carrier | TBPA | 6 | 6 | | | | | | |
| | HALS A | | | | | | | | |
| cosolvent | THF | | | | | | 60 | | |
| charge compensator | DNB | | 1 | | | | | | |
| | PB | | | | | | | | |
| Total (wt %) | | 100 | 100 | 100 | 100 | 100 | 100 | 100 | 100 |

Hybrid P/E compounds used in formulation #1 include S001 or a derivative thereof having different functional groups on the four peripheral thiophene rings, or S002 or a derivative thereof having different functional groups on the four benzene rings.

Hybrid P/E compounds used in formulation #2 include S054 or a derivative thereof having different functional groups on the four benzene rings.

Hybrid P/E compounds used in formulation #3 include S001 or a derivative thereof having different functional groups on the four peripheral thiophene rings, or S002 or S042 or a derivative thereof having different functional groups on the four benzene rings.

Hybrid P/E compounds used in formulation #4 include S001 or a derivative thereof having different functional groups on the four peripheral thiophene rings, or S054 or a derivative thereof having different functional groups on the four benzene rings.

Hybrid P/E compounds used in formulation #5 include S054 or a derivative thereof having different functional groups on the four benzene rings.

Chromophores used in formulation #6 include S001 or a derivative thereof having different functional groups on the four peripheral thiophene rings, or S054 or a derivative thereof having different functional groups on the four benzene rings.

Chromophores used in formulation #7 include S054 or a derivative thereof having different functional groups on the four benzene rings.

Chromophores used in formulation #8 include S042.
Chromophores used in formulation #9 include S001.

Example 6: Optical Properties of Hybrid P/E Switching Material

The VLT spectrum of formulation #3 comprising S001, S002 or S042, were determined for light and dark states. An Ocean Optics spectrometer was used to measure the % visible light transmittance of the sample, in its light and dark states, over an electromagnetic spectrum. The formulation is first exposed to UV light to switch to the dark state, decreasing the transmittance of the material in the visible range between about 400 and about 750 nm. An electric charge of 2 Volts is then applied to the switching material sample for 3 minutes, causing the sample to revert to its light state. In the light state, more light is permitted to pass through the switching material resulting in an increase in percent transmittance in the range from 400 to 750 nm. An exemplary spectra for S001 demonstrated a VLT in the light state of about 80%, and a VLT in the dark state was about 20%. This provided a contrast ratio of about 4.

Figure 12:
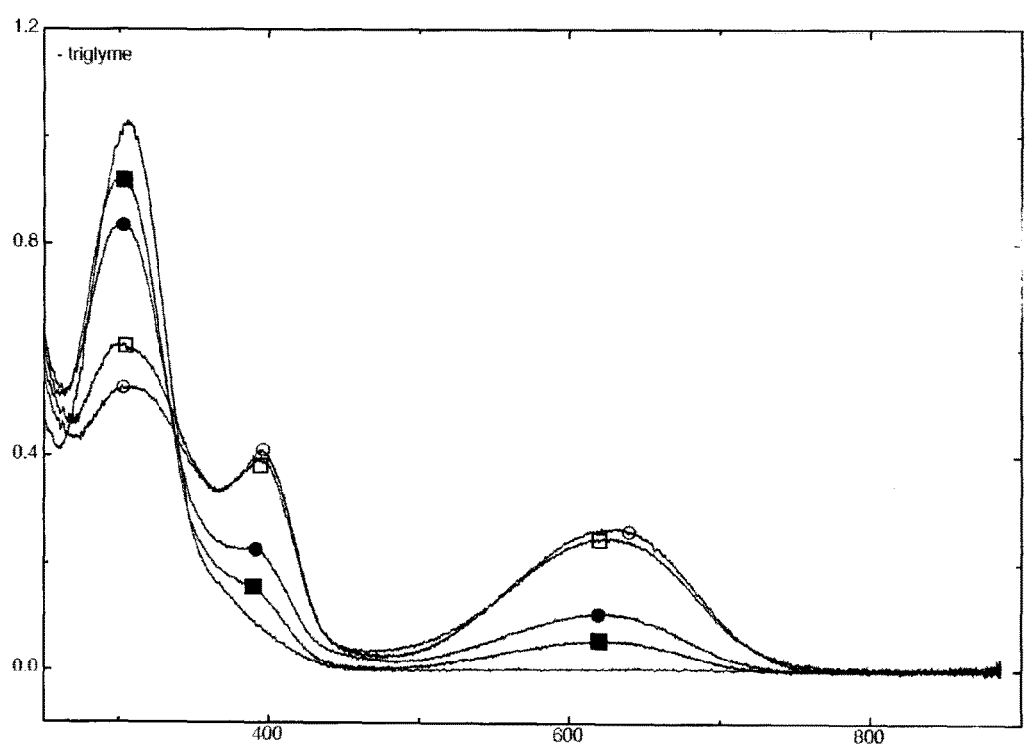
FIG. 12 is a graph showing the absorbance spectra of the hybrid photochromic/electrochromic switching material according to Formulation #2 comprising hybrid P/E compound S054 (in triglyme). Faded state (solid line); darkened using a 365 nm light source without (open circle) or with (open square) EnergyFilm™; and darkened using a solar simulator without (solid circle) or with (solid square) EnergyFilm™.

The sensitivity of the formulations to the intensity of UV light was also studied. Formulation #2 comprising hybrid P/E compound S054 was exposed to both UV light at 365 nm and solar radiation (using a solar simulator) with and without a UV blocking film made by Energy Film of Portland, Oreg. The Energy Film UV blocking film acts as a band-pass filter and effectively blocks the high intensity UV light (below about 365 nm). As illustrated in FIG. 12, depicting the absorbance spectra of the switching material under the various UV light intensities, the switching material maintains sensitivity to the low intensities of UV light (above about 365 nm) to darken. FIG. 12 shows a plot of the absorbance spectra in a faded state (solid line); darkened using a 365 nm light source without (open circle) or with (open square) EnergyFilm™; and darkened using a solar simulator without (solid circle) or with (solid square) EnergyFilm™. In a faded state (solid line), the absorbance of the formulation is reduced to baseline. Absorbance reaches a maximum at about 620-240 nm for all sample treatments, with the maximum absorbance varying with light source and presence or absence of a partial UV blocking layer. Highest absorbance is reached for a UV light source without EnergyFilm™—about 0.265. Placement of the UV blocking layer between the sample and light source reduces the maximum absorbance to about 0.254. Simulated full spectrum sunlight provides a maximum absorbance in the dark state of about 0.105; inclusion of the UV blocking layer reduces the maximum absorbance to about 0.055.

Example 7: Preparation of Variable Transmittance Optical Filters with Two Transparent Conductive Substrates Examples 7 to 16 as included herein pertain to the preparation and testing of variable transmittance optical filters comprising two transparent conductive substrates. The electrodes of these filters are not substantially co-planar, however, the variable transmittance optical filters themselves have been prepared with hybrid P/E switching materials and have been included to demonstrate general properties of the hybrid P/E switching materials in the format of this optical filter.

Method A:

An ITO coated PET substrate having a thickness of 7 mil (~178 microns) and a sheet resistance of 50 ohms/square (OC50, made by CP Films) is cut into two 15 cm×15 cm sheets. The substrate may be cleaned before use, and is temporarily laminated to glass plates to facilitate handling. Steel spacers are positioned at the perimeter of the PET, to set the gap for the final pressed device (from 20-70 microns). A volume of switching material (below, heated to facilitate dispensing), is placed on the PET to completely fill the gap between the PET sheets when the device is pressed. A second piece of glass-backed PET is placed on top, so that the PET sheets overlap such that there is some ITO coating exposed, to act as the external electrical contacts. The sandwich (glass-PET-switching material-PET-glass) is placed in the center of a press platens (heated to 45° C.). Pressure greater than 160 psi is applied to the filter using a Carver hydraulic press, or nip rollers, for a time sufficient to allow the switching material to attain a uniform thickness (at least 10 seconds, up to about a minute, or up to several hours). After the pressure is released, the glass plates are separated, any excess switching material is wiped off and conductive tape is applied to the exposed ITO. Total thickness of an optical filter (e.g ITO-coated PET+switching material) is about 16 mil (~406 microns), including a 2 mil (~51 microns) layer of switching material Method B:

An ITO coated PET substrate is prepared as described above. A switching material comprising a low-boiling solvent (THF) is then coated onto the conductive side of a first sheet of ITO-coated PET using a slot die, a knife coater, or other roll-to-roll coating method (according to manufacturer's instructions). The thickness of the coater is set such that the final coating once the low-boiling solvent is evaporated off is the desired thickness. For example, to obtain a final switching material thickness of about 50 microns, the initial wet coating may be set to about 114 microns. The low-boiling solvent is evaporated from the switching material using blown air or heat or a combination of both. A second layer of ITO-coated PET is laminated on top of the coating with the conductive side in contact with the switching material to form a sandwich structure. The laminated structure is cut to the desired size (if required) and electrical contacts added. An exemplary optical filter produced in this manner demonstrated a total thickness of about 16 mil (~406 microns), with a switching material layer of about 2 mil (~51 microns).

Example 8: Visible Light Transmittance (VLT) Determination of the Optical Filter The VLT of the optical filter prepared by the method A described in Example 7 comprising formulation #4 with S054 was measured using an Ocean Optics spectrometer. Optical filters exposed to 365 nm UV light for about 3 minutes had a VLT of 17%. The transmission increased after application of a charge of 2 Volts for about 3 minutes to 69%.

Example 9: Haze Determination of the Optical Filter

The clarity of the optical filter prepared by the method A described in Example 7 comprising formulation #4 with S054 or S001 was measured using a XL-211 Hazard Hazemeter manufactured by BYK Gardner. The haze of the optical filter was measured to be about 2%.

Example 10: Switching Speed Determination of the Optical Filter

Switching speed is determined by the amount of time it takes for the optical filter to go from the dark state to the light state, and vice versa. To transition from the light state to the dark state, the optical filter is exposed to 365 nm UV light for 3 minutes before application of voltage To transition from the dark state to the light state, a charge of 2 Volts is applied to the filter for 3 minutes, before exposure to the light source. Switching time from the light state to the dark state is measured as the time required to achieve 90% of the VL T of the dark state from the fully light state. Switching time from the dark state to the light state is measured as the time required to achieve 90% of the VLT of the light state, from the fully dark state.

The optical filter prepared by the method A described in Example 7 comprising switching material according to formulation #4 comprising S001 or 5054, the optical filter including a UV blocking film (Energy Film) applied to the glass-back PET opposite to the switching material, was tested. The switching speed of the optical filter was about 30 seconds from the light state to the dark state, and about 2 minutes for switching from the dark state to the light state. The switching speed of the optical filter prepared with formulation #1 comprising S001 or S002 was measured to be about 35 seconds from the dark state to the light state and 2 minutes from the light state to the dark state. The switching speed of the optical filter prepared with formulation #7 with S054, is measured to be about 3 minutes 20 seconds from the dark state to the light state and 12 seconds from the light state to the dark state. Thus, the switching time for transitioning from the light state to the dark state may, for some transition material comprising a hybrid P/E compound, be different from the switching time for transitioning from the dark state to the light state.

Example 11: Photostability Determination of the Optical Filter

Photostability of the optical filter is determined by exposing the samples to UV light similar to the UV light in the solar spectrum. Samples are tested at regular intervals to determine degradation. When the contrast ratio has dropped to 50% of the original contrast ratio of the device (determined prior to testing), the device is considered to have failed. The photostability of the optical filters is determined using a QUV accelerated weathering tester from Q-Labs. Photostability of the optical filter is also determined using an S16 accelerated testing instrument from Solar Light to test the photostability of the optical filter at higher power densities.

The photostability of the optical filter made according to the method described in Example 7 comprising formulation #5 using 5054 was tested on a QUV for 1300 hours at about 7.3 mW/cm$^2$ before 50% degradation was reached. The same optical filter was tested on a Solar Light unit at 135 mW/cm$^2$ for 540 hours before 50% degradation was reached.

Example 12: Cycling Durability Determination of the Optical Filter

Cycling durability is determined by exposing the optical filter to continuous UV light using a Spectroline transilluminator and applying a voltage to the optical filter at regular time intervals. First, the amount of time required to darken and lighten the optical filter is determined. This is then used to determine how much time the voltage should be turned on and off for in the automated test. Typically, the voltage "on" time is set to be the amount of time it takes for the optical filter to bleach to about 90% of its initial value. The voltage "off" time is set to be the amount of time it takes for the optical filter to darken to 90% of its original value. The cycling is then controlled by an automated cycling set-up using a PC, a LabJack instrument (available from LabJack Corporation of Lakewood Colo.). In the "off" state, the two electrodes are shorted together to dissipate the charge on the optical filter.

The cycling durability of the optical filter made according to the method described in Example 7 comprising formulation #6 comprising S054, with a UV blocking film (Energy Film) applied to the glass-backed PET opposite to the switching material, was tested. To observe the effect of ambient atmosphere on the durability of the device, a first preparation of the formulation (6-1) was prepared at the bench (exposed to ambient atmosphere), and a second preparation of the formulation (6-2 was prepared in an oxygen-free atmosphere (glove box). The optical filter comprising formulation 6-1 demonstrated 741 switching cycles before reaching a 50% degradation point (the contrast ratio decreased to 50% of the starting contrast ratio). In comparison, the optical filter comprising formulation 6-2 demonstrated 1553 cycles before reaching a 50% degradation point).

Example 13: Sheet Resistance Determination of the Optical Filter

The operability of optical filters using substrates of different sheet resistances was tested. Optical filters were made according to the method described in Example 7 comprising formulation #4 with S001 or S054, and ITO-coated substrates of 50 Ohms/square, 100 Ohms/square, and 300 Ohms/square. Optical filters were also made according to the method described in Example 6 comprising formulation #8 with S042, and ITO-coated substrates of 1,000 Ohms/square, and 100,000 Ohms/square. The optical filters were tested for the ability to transition between light and dark states. In all examples the optical filters were still able to lighten upon application of electricity. Optical filters with lower sheet resistances were observed to switch faster.

Example 14: Required Voltage Determination of the Optical Filter

To determine the minimal voltage required to cause the optical filters to switch from the dark state to the light state, incrementally higher voltages are applied until the device begins to transition from the dark to the light state. In an optical filter made according to the method described in Example 7 comprising formulation #4 with S001 or 5054, fading from the dark to light state is observed at about 1.8 Volts. The transitioning is faster at about 2 Volts. It has been observed that too high a voltage may not be desirable because other electrochemical reactions may be introduced that may cause fouling of the electrodes. For example, transitioning in the optical filter is impacted when a voltage greater than about 2.5 volts is applied, and brown spots are observed if the optical filters are left at that potential for a longer period of time.

Example 15: Impact of Optical Filter on Electrical Consumption and $CO_2$ Emissions The ability of a variable transmittance window of the present invention to provide significant energy and cost savings was determined. A building with variable transmittance insulated glass units was modeled using window and energy modeling software available from Lawrence Berkeley National Laboratories of Berkeley, Calif. The building modeled was a 400 square foot small office with a 0.9 wall-to window ratio. The building was modeled in five U.S. cities (Miami, Los Angeles, New York, Houston, and Chicago). The variable transmittance smart window used for the model was an insulating glass unit (IGU) with an optical filter laminated onto one of the panes, and a low emissivity coating on the inside of the exterior pane facing the sealed space. A variable transmittance window of this configuration was determined to achieve a solar heat gain coefficient (SHGC) of about 0.15 in the dark state, and about 0.32 in the light state. Using this variable transmittance window in the dark state resulted in average electricity savings of 28%, according to the model. The electricity savings resulted from a reduced requirement for air conditioning due to the variable transmittance windows. $CO_2$ emissions were reduced from about 19% to about 25%, due mostly to the reduction in electricity usage. The variable transmittance window of the model achieves a solar heat gain coefficient (SHGC) of about 0.15 with a corresponding percent visible light transmittance (VLT) of about 10% in the dark state. In the light state, the percent visible light transmittance of the variable transmittance window increases to about 58-60%, and the solar heat gain coefficient increases to 0.32. In the dark state, the variable transmittance window has a significantly lower solar heat gain coefficient than standard low-emissivity ("Low-E") glass. Standard Low-E glass in the same model achieves an SHGC of about 0.36, with a VLT of about 60-62%. Standard float glass (no coatings) in the same model achieves an SHGC of about 0.68, with a VLT of about 68%. Solarban 70XL Glass from PPG Industries (Pittsburgh, Pa.) in the same model achieves an SHGC of about 0.47, with a VLT of about 47%. The standard float glass has the highest (worst) solar heat gain coefficient while Solarban 70XL glass has the best SHGC of the non-dynamic glazings. The SHGC of an IGU using standard float glass is about 0.70 (according to the dataset included with the software). The SHGC of an IGU made using the Solarban 70XL glass is about 0.25 (according to the dataset provided with the software). The model demonstrates that an SHGC of less than 0.25 can be achieved with variable transmittance smart windows and dynamic glazings. In this example, the modeled variable transmittance window was assumed to have a contrast ratio of about six.

Example 16: Intermediate States of the Optical Filter

A prototype device made using formulation #3 comprising S001, S002 or S042 was tested for the ability to achieve intermediate states. The device is first darkened under UV light (365 nm) although solar light can equally be used. A DC voltage of about 2 Volts is then applied to the device for a short period of time (e.g., about 10% of the total switching time) before being switched off. During the time the power is applied the VLT of the device increases, but did not go all the way to the light state. Once the voltage is switched off, the device remains in its intermediate dark state without the need for any further application of power. If the voltage is turned on again, the device continues to transition to its light state.

Example 17: Photostability of Chromophores in Switching Materials of the Optical Filter The photostability of chromophores m various combinations of the switching material is tested by exposing the combination to UV light similar to the UV light in the solar spectrum. Optical filters comprising the combination are tested at regular intervals to determine degradation. When the contrast ratio of a device drops to 50% of the original contrast ratio (determined prior to testing), the device is considered to have failed. The photostability of an optical filter comprising the combination is determined using a QUV or QSUN accelerated weathering tester from Q-Labs, or an S 16 accelerated testing instrument from Solar Light (SL) to test the photostability of the combination at higher power densities.

Chromophores were tested in combination with various switching material components prepared according to Examples 5 and 7 and the results are shown in Table 4 below. Each chromophore was capable of achieving 700 hours in at least one of the combinations of switching material before 50% degradation was reached.

scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to," and the word "comprises" has a corresponding meaning. As used herein, the singular forms "a", "an" and "the" include plural referents unless the context clearly dictates otherwise. Citation of references herein shall not be construed as an admission that such references are prior art to the present invention. Citation of references herein does not constitute any admission as to the contents or date of the references. All publications are incorporated herein by reference as if each individual publication was specifically and individually indicated to be incorporated by reference herein and as though fully set forth herein. The invention includes all embodiments and variations substantially as hereinbefore described and with reference to the examples and drawings.

TABLE 4

Formulation and flexible devices tested. All devices employed EnergyFilm ™ UV blocker applied externally, save for Device #26. Device 25 included an additional acetate layer. All devices employed OC50 substrate Device #2 (graphene substrate). PB - 50 nm layer of Prussian blue electrochemically deposited on electrodes.

| | Device | | | Formulation | | | | | | |
|---|---|---|---|---|---|---|---|---|---|---|
| No. | Size (cm) | Thickness (μ) | Chromophore (%) | Polymer (%) | Solvent | Electrolyte (%) | Additives | method | avg int (mW/cm2) | Failure (hours) |
| 1 | 1.5 (ø) | 60 | S001(3) | PVB (25) | Triglyme | | | SL | 120 | 438 |
| 2 | 1.5 (ø) | 60 | S001(3) | PVB (25) | Triglyme | | | SL | 130 | 288 |
| 3 | 1.5 (ø) | 50 | S001(3) | PVB (25) | Triglyme | | | SL | 110 | 255 |
| 4 | 1.5 (ø) | 60 | S068(3) | PVB (25) | Triglyme | | | SL | 110 | 191 |
| 5 | 9 × 6 | 50 | S054(3.5) | PVB (25) | Triglyme | | | QUV | 9.8 | 1537 |
| 6 | 2.5 × 2.5 | 50 | S068(20) | PVB (25) | Triglyme | | | QUV | 9.8 | 1130 |
| 7 | 9 × 6 | 50 | S054(3) | PVB (25) | Tetraglyme | TBAPF6 (1) | | QUV | 9.8 | 1073 |
| 8 | 2.5 × 2.5 | 50 | S068(15) | PVB (25) | Triglyme | | | QUV | 9.8 | 1037 |
| 9 | 1.5 (ø) | 50 | S054(3.5) | PVB (20.2) | Triglyme | TBAPF6(1) | HALS A | SL | 95 | 104 |
| 10 | 2.5 × 2.5 | 50 | S068(10) | PVB (25) | Triglyme | | | QUV | 9.8 | 901 |
| 11 | 1.5 (ø) | 60 | S001(3) | PVB (25) | Triglyme | | | QUV | 9.8 | 865 |
| 12 | 1.5 (ø) | 50 | S054(3.5) | PVB (20.2) | Triglyme | TBAPF6 (1) | | SL | 110 | 76 |
| 13 | 3 × 5 | 50 | S054(3) | PVB (25) | Triglyme | | PB | QUV | 9.8 | 837 |
| 14 | 9 × 6 | 50 | S054(3) | PMMA (25) | Triglyme | | | QUV | 9.8 | 801 |
| 15 | 9 × 6 | 50 | S054(3) | PEMA (25) | Triglyme | | | QUV | 9.8 | 794 |
| 16 | 9 × 6 | 50 | S054(3) | PVB (25) | Triglyme | | | QUV | 9.8 | 787 |
| 17 | 1.5 (ø) | 60 | S068(3) | PVB (25) | Triglyme | | | QUV | 9.8 | 772 |
| 18 | 9 × 6 | 50 | S054(3) | PVB (25) | Tetraglyme | | | QUV | 9.8 | 636 |
| 19 | 9 × 6 | 50 | S054(2) | PVB (24) | Triglyme | TBAPF6 (1) | | QUV | 9.8 | 608 |
| 20 | 9 × 6 | 50 | S054(3.5) | PEMA (25) | Tetraglyme | TBAPF6 (1) | | QUV | 9.8 | 586 |
| 21 | 2.5 × 2.5 | 50 | S068(5) | PVB (25) | Triglyme | | | QUV | 9.8 | 572 |
| 22 | 9 × 6 | 50 | S054(3) | PMMA (25) | Tetraglyme | | | QUV | 9.8 | 543 |
| 23 | 3 × 5 | 50 | S054(3.5) | PVB (25) | Tetraglyme | TBAPF6 (1) | PB | QUV | 9.8 | 522 |
| 24 | 3 × 5 | 50 | S054(3.5) | PVB (25) | Tetraglyme | TBAPF6 (1) | | QUV | 9.8 | 522 |
| 25 | 3 × 5 | 50 | S054(6) | PVB (22) | Triglyme | TBAPF6 (1) | | Qsun | 5.6 | 688 |
| 26 | 7.5 × 7.5 | 50 | S054(5) | PVB (25) | Triglyme | | | QUV | 9.8 | 386 |
| 27 | 9 × 6 | 36 | S054(1.5) | PVB (24) | Triglyme | TBAPF6 (1) | | QUV | 9.8 | 358 |
| 28 | 9 × 6 | 25 | S054(2) | PVB (24) | Triglyme | TBAPF6 (1) | | QUV | 9.8 | 293 |
| 29 | 2.5 × 2.5 | 50 | S068(2.5) | PVB (25) | Triglyme | | | QUV | 9.8 | 136 |
| 30 | 9 × 6 | 50 | S054(1.7) | PMMA (25) | PC | | | QUV | 9.8 | 64 |
| 31 | 9 × 6 | 50 | S054(3.5) | PVB (25) | GBL | | | QUV | 9.8 | 21 |

Other Embodiments

The present invention has been described with regard to one or more embodiments. However, it will be apparent to persons skilled in the art that a number of variations and modifications can be made without departing from the scope of the invention as defined in the claims. Therefore, although various embodiments of the invention are disclosed herein, many adaptations and modifications may be made within the It is contemplated that any embodiment, aspect, example, method, composition, or element discussed in this specification may be implemented or combined in any suitable manner with any other embodiment, aspect, example, method, composition, or element.

Unless defined otherwise, all technical and scientific terms used herein have the same meaning as is commonly understood by one of ordinary skill in the art to which this invention belongs. If a definition set forth in this section is contrary to or otherwise inconsistent with a definition set forth in the patents, applications, published applications and other publications that are herein incorporated by reference, the definition set forth herein prevails over the definition that is incorporated herein by reference.

What is claimed is:

1. A variable transmittance optical filter comprising:
   a) a first layer comprising a first substantially transparent substrate with a substantially co-planar (SC) electrode system disposed thereon, the SC electrode system made of transparent electrically conductive material and comprising at least one pair of electrically separate electrodes arranged in a substantially co-planar manner on the first substantially transparent substrate, each pair of electrically separate electrodes comprising a first electrode and a second electrode,
   b) a second layer proximate to the first layer and comprising a transition material comprising a compound that is both photochromic and electrochromic, and that darkens in response to a non-electrical stimulus and lightens in response to application of an electric voltage; and
   c) an electrical connection system for electrically connecting the SC electrode system to a source of electric voltage, wherein the voltage to be applied to the first electrode and the second electrode is from about 0.5V to about 3.0V, or from about 1.2V to about 2.5V, or from about 1.8V to about 2.2V, or any amount or range therebetween.

2. The variable transmittance optical filter of claim 1, wherein the optical filter further comprises a second substantially transparent substrate.

3. The variable transmittance optical filter of claim 1, wherein the compound that is both photochromic and electrochromic is a diarylethene.

4. The variable transmittance optical filter of claim 1, wherein the first electrode and the second electrode of each pair comprise primary finger-like structures and the primary finger-like structures of the first electrode are interdigitated with the primary finger-like structures of the second electrode.

5. The variable transmittance optical filter of claim 4, wherein each of the primary finger-like structures comprises one or more secondary finger-like structures.

6. The variable transmittance optical filter of claim 5, wherein the one or more secondary finger-like structures of the first electrode are interdigitated with the one or more secondary finger-like structures of the second electrode.

7. A method of preparing a variable transmittance optical filter comprising the steps of:
   a) providing a first layer comprising a first substantially transparent substrate; and
      i. etching into a layer of substantially transparent electrically conductive material disposed thereon a substantially co-planar (SC) electrode system, the SC electrode system comprising at least one pair of electrically separate electrodes arranged in a substantially co-planar manner, each pair of electrically separate electrodes comprising a first electrode and a second electrode; or
      ii. printing onto the first substrate a substantially co-planar (SC) electrode system using a conductive ink, the SC electrode system comprising at least one pair of electrically separate electrodes arranged in a substantially co-planar manner, each pair of electrically separate electrodes comprising a first electrode and a second electrode;
   b) disposing a second layer proximate to the SC electrode system, the second layer comprising a transition material comprising a compound that is both photochromic and electrochromic that is capable of dynamically varying the degree of visible light transmittance on application of an electric voltage; and
   c) providing an electrical connection system electrically connecting the SC electrode system to a source of electric voltage, wherein the voltage to be applied to the first electrode and the second electrode is from about 0.5V to about 3.0V, or from about 1.2V to about 2.5V, or from about 1.8V to about 2.2V, or any amount or range therebetween.

8. The method of claim 7, wherein the variable transmittance optical filter further comprises a second substantially transparent substrate.

9. The method of claim 7, wherein the compound that is both photochromic and electrochromic is a diarylethene.

10. A variable transmittance optical filter comprising:
    a) a first layer comprising a first substantially transparent substrate with a substantially co-planar (SC) electrode system disposed thereon, the SC electrode system made of transparent electrically conductive material and comprising two or more pairs of electrically separate electrodes arranged in a substantially co-planar manner on the first substantially transparent substrate, each pair of electrically separate electrodes comprising a first electrode and a second electrode;
    b) a second layer proximate to the first layer and comprising a transition material that is capable of dynamically varying the degree of visible light transmittance on application of an electric voltage; and
    c) an electrical connection system for electrically connecting the SC electrode system to a source of electric voltage, wherein the voltage to be applied to the first electrode and the second electrode is from about 0.5V to about 3.0V, or from about 1.2V to about 2.5V, or from about 1.8V to about 2.2V, or any amount or range therebetween.

11. The variable transmittance optical filter of claim 10, wherein the transition material comprises a hybrid P/E (photochromic/electrochromic) compound.

12. The variable transmittance optical filter of claim 10, wherein after a positive voltage is applied to the first electrode and a negative voltage is applied to the second electrode, the polarity of the voltage applied to the first electrode and the second electrode is alternately reversed one or more times to transition a first state of visible light transmittance to a second state of visible light transmittance.

13. The variable transmittance optical filter of claim 12, wherein the transition material comprises a hybrid P/E (photochromic/electrochromic) compound.

14. A method of transitioning a transition material from a dark state to a faded state comprising:
    a) applying a positive voltage to a first electrode and a negative voltage to a second electrode, wherein the voltage applied to the first electrode is positive relative to the voltage applied to the second electrode, and wherein the voltage applied to the second electrode is negative relative to the voltage applied to first electrode; and
    b) reversing the polarity of the voltage, thereby applying a negative voltage to the first electrode and a positive voltage to the second electrode, wherein the voltage applied to the first electrode is negative relative to the voltage applied to second electrode, and wherein the voltage applied to the second electrode is positive relative to the voltage applied to first electrode, wherein the voltage applied to the first electrode and the second electrode is from about 0.5V to about 3.0V, or from about 1.2V to about 2.5V, or from about 1.8V to about 2.2V, or any amount or range therebetween.

15. The method of claim 14, wherein the transition material comprises a hybrid P/E (photochromic/electrochromic) compound.

* * * * *